US012569255B2

(12) United States Patent
Fago et al.

(10) Patent No.: US 12,569,255 B2
(45) Date of Patent: Mar. 10, 2026

(54) OCCLUSION CLIP

(71) Applicant: AtriCure, Inc., Mason, OH (US)

(72) Inventors: Frank M. Fago, Mason, OH (US); Kimberly Gray, Florence, KY (US)

(73) Assignee: AtriCure, Inc., Mason, OH (US)

( * ) Notice: Subject to any disclaimer, the term of this patent is extended or adjusted under 35 U.S.C. 154(b) by 0 days.

(21) Appl. No.: 18/770,505

(22) Filed: Jul. 11, 2024

(65) Prior Publication Data

US 2024/0358377 A1 Oct. 31, 2024

Related U.S. Application Data

(63) Continuation of application No. 17/841,760, filed on Jun. 16, 2022, which is a continuation of application (Continued)

(51) Int. Cl.
*A61B 17/122* (2006.01)
*A61B 17/00* (2006.01)
(Continued)

(52) U.S. Cl.
CPC .............................. *A61B 17/1227* (2013.01); *A61B 2017/00526* (2013.01); *A61B 2017/00884* (2013.01);
(Continued)

(58) Field of Classification Search
CPC ... A61B 17/1227; A61B 17/08; A61B 17/083; A61B 17/12; A61B 17/122; A61B 2017/00884
See application file for complete search history.

(56) References Cited

U.S. PATENT DOCUMENTS

| | | | |
|---|---|---|---|
| 119,938 | A | 10/1871 | Mellish |
| 1,152,492 | A | 9/1915 | Deming |

(Continued)

FOREIGN PATENT DOCUMENTS

| | | |
|---|---|---|
| CN | 2712287 Y | 7/2005 |
| CN | 2875334 Y | 3/2007 |

(Continued)

OTHER PUBLICATIONS

Al-Saady et al., "Left atrial appendage: structure, function, and role in thromboembolism" Heart (1999) 82:547-555, St. George's Hosp Med School, London UK.

(Continued)

*Primary Examiner* — Julian W Woo
(74) *Attorney, Agent, or Firm* — Dorton & Willis LLP; Ryan Willis

(57) ABSTRACT

An occlusion clip comprising: (a) a first elongated occlusion arm; (b) a second elongated occlusion arm; (c) a first elongated biasing arm coupled to a distal portion of the first elongated occlusion arm; (d) a second elongated biasing arm coupled to a distal portion of the second elongated biasing arm is coupled to a proximal portion of the second elongated biasing arm, where the first elongated occlusion arm extends parallel to the first elongated bias arm along a majority of its length, and where the second elongated occlusion arm extends parallel to the second elongated bias arm along a majority of its length.

18 Claims, 6 Drawing Sheets

Related U.S. Application Data

No. 15/868,270, filed on Jan. 11, 2018, now Pat. No. 11,389,175, which is a continuation of application No. 14/964,930, filed on Dec. 10, 2015, now Pat. No. 9,901,352.

(60) Provisional application No. 62/091,230, filed on Dec. 12, 2014.

(51) Int. Cl.
*A61B 17/08* (2006.01)
*A61B 17/12* (2006.01)

(52) U.S. Cl.
CPC ............ *A61B 17/08* (2013.01); *A61B 17/083* (2013.01); *A61B 17/12* (2013.01); *A61B 17/122* (2013.01)

(56) References Cited

U.S. PATENT DOCUMENTS

| | | | |
|---|---|---|---|
| 1,162,578 A | 11/1915 | Forge | |
| 1,205,889 A | 11/1916 | Halvorson | |
| 1,357,233 A | 11/1920 | William | |
| 1,491,941 A | 4/1924 | Wood | |
| 1,684,721 A | 9/1928 | Wood | |
| 1,915,229 A | 6/1933 | Henry, Jr. | |
| 2,051,174 A | 8/1936 | Martin | |
| 2,060,724 A | 11/1936 | Carroll | |
| 2,108,325 A * | 2/1938 | Ziegler | A61B 17/128 |
| | | | 606/120 |
| 2,371,978 A | 3/1945 | Perham | |
| 2,384,697 A | 9/1945 | Peter | |
| 2,540,722 A | 2/1951 | Gardner | |
| 2,593,201 A | 4/1952 | Saunders | |
| 2,815,557 A | 12/1957 | Jorgensen | |
| 3,032,039 A | 5/1962 | Beaty | |
| 3,496,932 A | 2/1970 | Prisk et al. | |
| 3,503,396 A | 3/1970 | Pierie et al. | |
| 3,503,398 A | 3/1970 | Fogarty et al. | |
| 3,579,751 A | 5/1971 | Jonckheere | |
| 3,682,180 A | 8/1972 | Mcfarlane | |
| 3,818,784 A | 6/1974 | Mc | |
| 3,854,482 A | 12/1974 | Laugherty et al. | |
| 3,856,016 A | 12/1974 | Davis | |
| 3,856,017 A | 12/1974 | Chancholle et al. | |
| 3,856,018 A | 12/1974 | Perisse et al. | |
| 3,954,108 A | 5/1976 | Davis | |
| 4,120,302 A | 10/1978 | Ziegler | |
| 4,226,239 A | 10/1980 | Polk et al. | |
| 4,231,360 A | 11/1980 | Zloczysti et al. | |
| 4,274,415 A | 6/1981 | Kanamoto et al. | |
| 4,428,374 A | 1/1984 | Auburn | |
| 4,493,319 A | 1/1985 | Polk et al. | |
| 4,552,128 A | 11/1985 | Haber | |
| RE32,269 E | 10/1986 | Bisk et al. | |
| 4,716,634 A | 1/1988 | Fan | |
| 4,788,966 A | 12/1988 | Yoon | |
| 4,791,707 A | 12/1988 | Tucker | |
| 4,821,719 A | 4/1989 | Fogarty | |
| 4,869,268 A | 9/1989 | Yoon | |
| 4,917,677 A | 4/1990 | McCarthy | |
| 4,950,284 A | 8/1990 | Green et al. | |
| 4,961,743 A | 10/1990 | Kees, Jr. et al. | |
| 4,966,603 A | 10/1990 | Focelle et al. | |
| 5,026,379 A | 6/1991 | Yoon | |
| 5,063,645 A | 11/1991 | Crespo | |
| 5,075,935 A | 12/1991 | Abdi | |
| 5,100,416 A | 3/1992 | Oh et al. | |
| 5,108,420 A | 4/1992 | Marks | |
| 5,119,804 A | 6/1992 | Anstadt | |
| 5,171,250 A | 12/1992 | Yoon | |
| 5,171,252 A | 12/1992 | Friedland | |
| 5,190,541 A | 3/1993 | Abele et al. | |
| 5,217,030 A | 6/1993 | Yoon | |
| 5,217,473 A | 6/1993 | Yoon | |
| 5,258,000 A | 11/1993 | Gianturco | |
| 5,282,811 A | 2/1994 | Booker et al. | |
| 5,282,829 A | 2/1994 | Hermes | |
| 5,282,844 A | 2/1994 | Stokes et al. | |
| 5,290,299 A | 3/1994 | Fain et al. | |
| 5,306,234 A | 4/1994 | Johnson | |
| 5,309,927 A | 5/1994 | Welch | |
| 5,334,209 A | 8/1994 | Yoon | |
| 5,336,252 A | 8/1994 | Cohen | |
| 5,342,373 A | 8/1994 | Stefanchik et al. | |
| 5,366,459 A | 11/1994 | Yoon | |
| 5,402,558 A | 4/1995 | Santapa | |
| 5,403,311 A | 4/1995 | Abele et al. | |
| 5,403,343 A | 4/1995 | Sugarbaker | |
| 5,425,740 A | 6/1995 | Hutchinson, Jr. | |
| 5,439,156 A | 8/1995 | Grant et al. | |
| 5,441,193 A | 8/1995 | Gravener | |
| 5,445,167 A | 8/1995 | Yoon et al. | |
| 5,452,733 A | 9/1995 | Sterman et al. | |
| 5,487,746 A * | 1/1996 | Yu | A61B 17/122 |
| | | | 24/703.1 |
| 5,549,628 A | 8/1996 | Cooper et al. | |
| 5,575,795 A | 11/1996 | Anderson | |
| 5,582,616 A | 12/1996 | Bolduc et al. | |
| 5,593,414 A | 1/1997 | Shipp et al. | |
| 5,609,599 A | 3/1997 | Levin | |
| 5,620,452 A | 4/1997 | Yoon | |
| 5,634,932 A | 6/1997 | Schmidt | |
| 5,643,255 A | 7/1997 | Organ | |
| 5,643,291 A | 7/1997 | Pier et al. | |
| 5,653,720 A | 8/1997 | Johnson et al. | |
| 5,665,100 A | 9/1997 | Yoon | |
| 5,667,518 A | 9/1997 | Pannell | |
| 5,676,636 A | 10/1997 | Chin | |
| 5,681,330 A | 10/1997 | Hughett et al. | |
| 5,683,405 A | 11/1997 | Yacoubian et al. | |
| 5,695,505 A | 12/1997 | Yoon | |
| 5,702,411 A | 12/1997 | Back et al. | |
| 5,707,377 A | 1/1998 | Keller et al. | |
| 5,709,224 A | 1/1998 | Behl et al. | |
| 5,727,569 A | 3/1998 | Benetti et al. | |
| 5,728,121 A | 3/1998 | Bimbo et al. | |
| 5,733,295 A | 3/1998 | Back et al. | |
| 5,735,848 A | 4/1998 | Yates et al. | |
| 5,758,420 A | 6/1998 | Schmidt et al. | |
| 5,762,255 A | 6/1998 | Chrisman et al. | |
| 5,766,217 A | 6/1998 | Christy | |
| 5,782,397 A | 7/1998 | Koukline | |
| 5,782,844 A | 7/1998 | Yoon et al. | |
| 5,797,960 A | 8/1998 | Stevens et al. | |
| 5,810,851 A | 9/1998 | Yoon | |
| 5,810,882 A | 9/1998 | Bolduc et al. | |
| 5,823,956 A | 10/1998 | Roth et al. | |
| 5,824,008 A | 10/1998 | Bolduc et al. | |
| 5,827,216 A | 10/1998 | Igo et al. | |
| 5,827,306 A | 10/1998 | Yoon | |
| 5,830,221 A | 11/1998 | Stein et al. | |
| 5,833,700 A | 11/1998 | Fogelberg et al. | |
| 5,843,101 A | 12/1998 | Fry | |
| 5,843,121 A | 12/1998 | Yoon | |
| 5,843,152 A | 12/1998 | Tu et al. | |
| 5,849,019 A | 12/1998 | Yoon | |
| 5,865,791 A | 2/1999 | Whayne et al. | |
| 5,891,162 A | 4/1999 | Sugarbaker et al. | |
| 5,893,863 A | 4/1999 | Yoon | |
| 5,919,202 A | 7/1999 | Yoon | |
| 5,921,997 A | 7/1999 | Fogelberg et al. | |
| 5,922,001 A | 7/1999 | Yoon | |
| 5,922,002 A | 7/1999 | Yoon | |
| 5,964,772 A | 10/1999 | Bolduc et al. | |
| 5,984,917 A | 11/1999 | Fleischman et al. | |
| 5,984,938 A | 11/1999 | Yoon | |
| 5,984,939 A | 11/1999 | Yoon | |
| 6,007,552 A | 12/1999 | Fogarty et al. | |
| 6,016,452 A | 1/2000 | Kasevich | |
| 6,019,722 A | 2/2000 | Spence et al. | |
| 6,023,818 A | 2/2000 | Shang | |
| 6,042,563 A | 3/2000 | Morejohn et al. | |

(56) References Cited

U.S. PATENT DOCUMENTS

| | | | |
|---|---|---|---|
| 6,045,571 A | 4/2000 | Hill et al. |
| 6,074,418 A | 6/2000 | Buchanan et al. |
| 6,077,261 A | 6/2000 | Behl et al. |
| 6,080,173 A | 6/2000 | Williamson, IV et al. |
| 6,088,889 A | 7/2000 | Luther et al. |
| 6,096,052 A | 8/2000 | Callister et al. |
| 6,099,539 A | 8/2000 | Howell et al. |
| 6,099,550 A | 8/2000 | Yoon |
| 6,152,144 A | 11/2000 | Lesh et al. |
| 6,152,936 A | 11/2000 | Christy et al. |
| 6,161,543 A | 12/2000 | Cox et al. |
| 6,165,183 A | 12/2000 | Kuehn et al. |
| 6,179,850 B1 | 1/2001 | Goradia |
| 6,193,732 B1 | 2/2001 | Frantzen et al. |
| 6,203,541 B1 | 3/2001 | Keppel |
| 6,231,561 B1 | 5/2001 | Frazier et al. |
| 6,237,605 B1 | 5/2001 | Vaska et al. |
| 6,241,727 B1 | 6/2001 | Tu et al. |
| 6,248,124 B1 | 6/2001 | Pedros et al. |
| 6,258,105 B1 | 7/2001 | Hart et al. |
| 6,270,516 B1 | 8/2001 | Tanner et al. |
| 6,277,065 B1 | 8/2001 | Donofrio |
| 6,280,415 B1 | 8/2001 | Johnson |
| 6,290,674 B1 | 9/2001 | Roue et al. |
| 6,296,656 B1 | 10/2001 | Bolduc et al. |
| 6,299,612 B1 | 10/2001 | Ouchi |
| 6,312,447 B1 | 11/2001 | Grimes |
| 6,315,715 B1 | 11/2001 | Taylor et al. |
| 6,322,494 B1 | 11/2001 | Bullivant et al. |
| 6,328,688 B1 | 12/2001 | Borst et al. |
| 6,330,964 B1 | 12/2001 | Kayan et al. |
| 6,334,843 B1 | 1/2002 | Borst et al. |
| 6,336,898 B1 | 1/2002 | Borst et al. |
| 6,340,344 B1 | 1/2002 | Christopher |
| 6,357,100 B2 | 3/2002 | Speller, Jr. et al. |
| 6,387,105 B1 | 5/2002 | Gifford, III et al. |
| 6,402,765 B1 | 6/2002 | Monassevitch et al. |
| 6,416,554 B1 | 7/2002 | Alferness et al. |
| 6,428,548 B1 | 8/2002 | Durgin et al. |
| 6,436,088 B2 | 8/2002 | Frazier et al. |
| 6,447,542 B1 | 9/2002 | Weadock |
| 6,450,391 B1 | 9/2002 | Kayan et al. |
| 6,464,700 B1 | 10/2002 | Koblish et al. |
| 6,465,196 B1 | 10/2002 | Hobbs et al. |
| 6,485,407 B2 | 11/2002 | Alferness et al. |
| 6,488,689 B1 | 12/2002 | Kaplan et al. |
| 6,491,701 B2 | 12/2002 | Tierney et al. |
| 6,491,706 B1 | 12/2002 | Alferness et al. |
| 6,494,211 B1 | 12/2002 | Boyd et al. |
| 6,506,149 B2 | 1/2003 | Peng et al. |
| 6,508,829 B1 | 1/2003 | Levinson et al. |
| 6,514,265 B2 | 2/2003 | Ho et al. |
| 6,520,974 B2 | 2/2003 | Tanner et al. |
| 6,562,051 B1 | 5/2003 | Bolduc et al. |
| 6,578,585 B1 | 6/2003 | Stachowski et al. |
| 6,579,304 B1 | 6/2003 | Hart et al. |
| 6,584,360 B2 | 6/2003 | Francischelli et al. |
| 6,607,504 B2 | 8/2003 | Haarala et al. |
| 6,607,542 B1 | 8/2003 | Wild |
| 6,610,074 B2 | 8/2003 | Santilli |
| 6,645,196 B1 | 11/2003 | Nixon et al. |
| 6,652,515 B1 | 11/2003 | Maguire et al. |
| 6,666,861 B1 | 12/2003 | Grabek |
| 6,676,684 B1 | 1/2004 | Morley et al. |
| 6,679,268 B2 | 1/2004 | Stevens et al. |
| 6,701,929 B2 | 3/2004 | Hussein |
| 6,709,442 B2 | 3/2004 | Miller et al. |
| 6,712,804 B2 | 3/2004 | Roue et al. |
| 6,719,767 B1 | 4/2004 | Kimblad |
| 6,746,461 B2 | 6/2004 | Fry |
| 6,770,081 B1 | 8/2004 | Cooper et al. |
| 6,793,664 B2 | 9/2004 | Mazzocchi et al. |
| 6,849,075 B2 | 2/2005 | Bertolero et al. |
| 6,849,078 B2 | 2/2005 | Durgin et al. |
| 6,872,210 B2 | 3/2005 | Hearn |
| 6,896,684 B2 | 5/2005 | Monassevitch et al. |
| 6,911,032 B2 | 6/2005 | Jugenheimer et al. |
| 6,955,175 B2 | 10/2005 | Stevens et al. |
| 6,955,643 B2 | 10/2005 | Gellman et al. |
| 6,960,218 B2 | 11/2005 | Rennich |
| 6,981,628 B2 | 1/2006 | Wales |
| 7,008,401 B2 | 3/2006 | Thompson et al. |
| 7,011,669 B2 | 3/2006 | Kimblad |
| 7,033,378 B2 | 4/2006 | Smith et al. |
| 7,044,134 B2 | 5/2006 | Khairkhahan et al. |
| 7,056,294 B2 | 6/2006 | Khairkhahan et al. |
| 7,077,851 B2 | 7/2006 | Lutze et al. |
| 7,113,831 B2 | 9/2006 | Hooven |
| 7,118,582 B1 | 10/2006 | Wang et al. |
| 7,169,164 B2 | 1/2007 | Borillo et al. |
| 7,207,997 B2 | 4/2007 | Shipp et al. |
| 7,209,783 B2 | 4/2007 | Fellows et al. |
| 7,226,458 B2 | 6/2007 | Kaplan et al. |
| 7,250,195 B1 | 7/2007 | Storey et al. |
| 7,318,829 B2 | 1/2008 | Kaplan et al. |
| 7,344,543 B2 | 3/2008 | Sra |
| 7,424,965 B2 | 9/2008 | Racenet et al. |
| 7,473,261 B2 | 1/2009 | Rennich |
| 7,527,634 B2 | 5/2009 | Zenati et al. |
| 7,572,266 B2 | 8/2009 | Young et al. |
| 7,644,848 B2 | 1/2010 | Swayze et al. |
| 7,862,571 B2 | 1/2011 | Dennis |
| 7,881,762 B2 | 2/2011 | Kling et al. |
| 7,892,244 B2 | 2/2011 | Monassevitch et al. |
| 7,896,895 B2 | 3/2011 | Boudreaux et al. |
| 8,172,870 B2 | 5/2012 | Shipp |
| 8,201,310 B1 | 6/2012 | Abdi et al. |
| 8,313,508 B2 | 11/2012 | Belson et al. |
| 8,578,571 B2 | 11/2013 | Schmidt et al. |
| 8,636,754 B2 | 1/2014 | Hughett, Sr. et al. |
| 8,852,218 B2 | 10/2014 | Hughett, Sr. et al. |
| 8,979,876 B2 | 3/2015 | Kassab et al. |
| 9,017,349 B2 | 4/2015 | Privitera et al. |
| 9,089,391 B2 | 7/2015 | Kassab et al. |
| 9,393,023 B2 | 7/2016 | Privitera et al. |
| 9,737,213 B1 | 8/2017 | Heaton, II et al. |
| 9,883,863 B2 | 2/2018 | Hughett, Sr. et al. |
| 9,901,351 B2 | 2/2018 | Winkler et al. |
| 9,901,352 B2 | 2/2018 | Fago et al. |
| 10,166,024 B2 | 1/2019 | Williamson, IV et al. |
| 10,433,854 B2 | 10/2019 | Miller et al. |
| 10,898,204 B2 | 1/2021 | Winkler et al. |
| 11,266,413 B2 | 3/2022 | Winkler et al. |
| 11,389,175 B2 | 7/2022 | Fago et al. |
| 11,471,161 B2 | 10/2022 | Hughett, Sr. et al. |
| 11,883,035 B2 | 1/2024 | Privitera et al. |
| 11,911,042 B2 | 2/2024 | Winkler et al. |
| 11,925,355 B2 | 3/2024 | Winkler et al. |
| 11,998,211 B2 | 6/2024 | Winkler et al. |
| 11,998,212 B2 | 6/2024 | Winkler et al. |
| 12,004,752 B2 | 6/2024 | Winkler et al. |
| 12,076,019 B2 | 9/2024 | Winkler et al. |
| 2001/0005787 A1 | 6/2001 | Oz et al. |
| 2001/0029384 A1 | 10/2001 | Nicholas et al. |
| 2001/0039419 A1 | 11/2001 | Francischelli et al. |
| 2001/0039434 A1 | 11/2001 | Frazier et al. |
| 2001/0039435 A1 | 11/2001 | Roue et al. |
| 2002/0013605 A1 | 1/2002 | Bolduc et al. |
| 2002/0022860 A1 | 2/2002 | Borillo et al. |
| 2002/0026214 A1 | 2/2002 | Tanner et al. |
| 2002/0026216 A1 | 2/2002 | Grimes |
| 2002/0032454 A1 | 3/2002 | Durgin et al. |
| 2002/0035374 A1 | 3/2002 | Borillo et al. |
| 2002/0049457 A1 | 4/2002 | Kaplan et al. |
| 2002/0055750 A1 | 5/2002 | Durgin et al. |
| 2002/0058967 A1 | 5/2002 | Jervis |
| 2002/0062130 A1 | 5/2002 | Jugenheimer et al. |
| 2002/0065524 A1 | 5/2002 | Miller et al. |
| 2002/0077660 A1 | 6/2002 | Kayan et al. |
| 2002/0099390 A1 | 7/2002 | Kaplan et al. |
| 2002/0103492 A1 | 8/2002 | Kaplan et al. |
| 2002/0111637 A1 | 8/2002 | Kaplan et al. |
| 2002/0111641 A1 | 8/2002 | Peterson et al. |
| 2002/0111643 A1 | 8/2002 | Herrmann et al. |

(56) References Cited

U.S. PATENT DOCUMENTS

| | | |
|---|---|---|
| 2002/0111647 A1 | 8/2002 | Khairkhahan et al. |
| 2002/0169377 A1 | 11/2002 | Khairkhahan et al. |
| 2002/0177859 A1 | 11/2002 | Monassevitch et al. |
| 2002/0177862 A1 | 11/2002 | Aranyi et al. |
| 2002/0183768 A1 | 12/2002 | Deem et al. |
| 2003/0009441 A1 | 1/2003 | Holsten et al. |
| 2003/0018362 A1 | 1/2003 | Fellows et al. |
| 2003/0023248 A1 | 1/2003 | Parodi |
| 2003/0023266 A1 | 1/2003 | Borillo et al. |
| 2003/0055422 A1 | 3/2003 | Lesh |
| 2003/0083677 A1 | 5/2003 | Damarati |
| 2003/0158464 A1 | 8/2003 | Bertolero |
| 2004/0030335 A1 | 2/2004 | Zenati et al. |
| 2004/0064138 A1 | 4/2004 | Grabek |
| 2004/0073241 A1 | 4/2004 | Barry et al. |
| 2004/0097982 A1 | 5/2004 | Jugenheimer et al. |
| 2004/0215216 A1 | 10/2004 | Gannoe et al. |
| 2005/0021062 A1 | 1/2005 | Dennis |
| 2005/0085808 A1 | 4/2005 | Nakao |
| 2005/0149068 A1 | 7/2005 | Williams et al. |
| 2005/0149069 A1 | 7/2005 | Bertolero et al. |
| 2005/0203561 A1 | 9/2005 | Palmer et al. |
| 2005/0240219 A1 | 10/2005 | Kahle et al. |
| 2005/0251183 A1 | 11/2005 | Buckman et al. |
| 2005/0277959 A1 | 12/2005 | Cosgrove et al. |
| 2006/0020271 A1 | 1/2006 | Stewart et al. |
| 2006/0084974 A1 | 4/2006 | Privitera et al. |
| 2006/0100646 A1 | 5/2006 | Hart et al. |
| 2006/0100649 A1 | 5/2006 | Hart |
| 2006/0161147 A1 | 7/2006 | Privitera et al. |
| 2006/0161149 A1 | 7/2006 | Privitera et al. |
| 2006/0212049 A1 | 9/2006 | Mohiuddin |
| 2006/0229594 A1 | 10/2006 | Francischelli et al. |
| 2006/0253129 A1 | 11/2006 | Liddicoat et al. |
| 2006/0271089 A1 | 11/2006 | Alejandro et al. |
| 2007/0016228 A1 | 1/2007 | Salas |
| 2007/0021761 A1 | 1/2007 | Phillips |
| 2007/0027456 A1 | 2/2007 | Gartner et al. |
| 2007/0032807 A1 | 2/2007 | Ortiz et al. |
| 2007/0149988 A1 | 6/2007 | Michler et al. |
| 2007/0149989 A1 | 6/2007 | Santilli et al. |
| 2007/0213585 A1 | 9/2007 | Monassevitch et al. |
| 2007/0213747 A1 | 9/2007 | Monassevitch et al. |
| 2008/0004637 A1 | 1/2008 | Klassen et al. |
| 2008/0033457 A1 | 2/2008 | Francischelli et al. |
| 2008/0039879 A1 | 2/2008 | Chin et al. |
| 2008/0125795 A1 | 5/2008 | Kaplan et al. |
| 2008/0208324 A1 | 8/2008 | Glithero et al. |
| 2008/0230971 A1 | 9/2008 | Farooqui |
| 2008/0244880 A1 | 10/2008 | Rankin et al. |
| 2009/0012545 A1 | 1/2009 | Williamson, IV et al. |
| 2009/0069823 A1 | 3/2009 | Foerster et al. |
| 2009/0209986 A1 | 8/2009 | Stewart et al. |
| 2009/0240266 A1 | 9/2009 | Dennis |
| 2009/0253961 A1 | 10/2009 | Le et al. |
| 2010/0004504 A1 | 1/2010 | Callas et al. |
| 2010/0004663 A1 | 1/2010 | Murphy et al. |
| 2010/0114124 A1 | 5/2010 | Kelleher et al. |
| 2010/0179570 A1 | 7/2010 | Privitera et al. |
| 2010/0204716 A1 | 8/2010 | Stewart et al. |
| 2010/0298849 A1 | 11/2010 | Lazic |
| 2011/0029028 A1 | 2/2011 | Peters et al. |
| 2011/0046437 A1 | 2/2011 | Kassab et al. |
| 2011/0046641 A1 | 2/2011 | Kassab et al. |
| 2011/0152922 A1 | 6/2011 | Jeong |
| 2011/0224700 A1 | 9/2011 | Schmidt et al. |
| 2011/0288571 A1 | 11/2011 | Steinhilper et al. |
| 2011/0313437 A1 | 12/2011 | Yeh |
| 2012/0035622 A1 | 2/2012 | Kiser et al. |
| 2012/0035631 A1 | 2/2012 | Hughett, Sr. et al. |
| 2012/0109161 A1 | 5/2012 | Privitera et al. |
| 2012/0149990 A1 | 6/2012 | Buehler et al. |
| 2014/0058411 A1 | 2/2014 | Soutorine et al. |
| 2014/0142597 A1 | 5/2014 | Winkler et al. |
| 2014/0172084 A1 | 6/2014 | Callas et al. |
| 2014/0222033 A1 | 8/2014 | Foerster et al. |
| 2014/0259629 A1 | 9/2014 | Dion et al. |
| 2014/0309671 A1 | 10/2014 | Basic et al. |
| 2014/0358168 A1 | 12/2014 | Hughett, Sr. et al. |
| 2015/0057684 A1 | 2/2015 | Zieris |
| 2015/0374380 A1 | 12/2015 | Miller et al. |
| 2016/0008001 A1 | 1/2016 | Winkler et al. |
| 2018/0199944 A1 | 7/2018 | Hughett, Sr. et al. |
| 2018/0317922 A1 | 11/2018 | Winkler et al. |
| 2019/0357912 A1 | 11/2019 | Privitera et al. |
| 2021/0106336 A1 | 4/2021 | Winkler et al. |
| 2022/0304694 A1 | 9/2022 | Fago et al. |
| 2023/0009892 A1 | 1/2023 | Winkler et al. |
| 2023/0023804 A1 | 1/2023 | Hughett, Sr. et al. |
| 2023/0338031 A1 | 10/2023 | Winkler et al. |
| 2023/0338032 A1 | 10/2023 | Winkler et al. |
| 2023/0338033 A1 | 10/2023 | Winkler et al. |
| 2023/0338040 A1 | 10/2023 | Winkler et al. |
| 2023/0338041 A1 | 10/2023 | Winkler et al. |
| 2023/0338043 A1 | 10/2023 | Privitera et al. |
| 2023/0389928 A1 | 12/2023 | Hughett et al. |
| 2024/0130735 A1 | 4/2024 | Privitera et al. |

FOREIGN PATENT DOCUMENTS

| | | |
|---|---|---|
| CN | 201510318 U | 6/2010 |
| EP | 1584293 A1 | 10/2005 |
| EP | 1600108 A2 | 11/2005 |
| EP | 3068313 A1 | 9/2016 |
| RU | 2275870 C2 | 5/2006 |
| WO | WO-9315791 A1 | 8/1993 |
| WO | WO-9415535 A1 | 7/1994 |
| WO | WO-9818389 A1 | 5/1998 |
| WO | WO-9824488 A2 | 6/1998 |
| WO | WO-9913785 A1 | 3/1999 |
| WO | WO-9913936 A1 | 3/1999 |
| WO | WO-9962409 A1 | 12/1999 |
| WO | WO-0135832 A2 | 5/2001 |
| WO | WO-0197696 A1 | 12/2001 |
| WO | WO-03011150 A1 | 2/2003 |
| WO | WO-03096881 A2 | 11/2003 |
| WO | WO-2006009729 A2 | 1/2006 |
| WO | WO-2007009099 A2 | 1/2007 |
| WO | WO-2007019268 A2 | 2/2007 |
| WO | WO-2006009729 A3 | 5/2007 |
| WO | WO-2007093198 A1 | 8/2007 |
| WO | WO-2007102152 A2 | 9/2007 |
| WO | WO-2007127664 A1 | 11/2007 |
| WO | WO-2010011661 A1 | 1/2010 |
| WO | WO-2010099437 A1 | 9/2010 |
| WO | WO-2012075532 A1 | 6/2012 |
| WO | WO-2013025841 A1 | 2/2013 |
| WO | WO-2013110089 A1 | 7/2013 |
| WO | WO-2015077528 A1 | 5/2015 |
| WO | WO-2016094647 A1 | 6/2016 |

OTHER PUBLICATIONS

Aytac et 1., "Intrapericardial aneurysm of the left atrial appendix" J. Cardiovas. Surg., 21, 1980, pp. 509-511.

Blackshear, J.L. et al., (Feb. 1996). "Appendage Obliteration to Reduce Stroke in Cardiac Surgical Patients With Atrial Fibrillation," Ann. Thorac. Surg. 61(2), 755-9, 13 pages.

Blackshear, J.L. et al. (Oct. 1, 2003). "Thorascopic Extracardiac Obliteration of the Left Atrial Appendage for Stroke Risk Reduction in Atrial Fibrillation," J. Am. Coll. Cardiol. 42(7):1249-1252.

Burke, R.P. et al. (1992). "Improved Surgical Approach to Left Atrial Appendage Aneurysm," Journal of Cardiac Surgery 7(2):104-107.

Coffin, L.H. (Jun. 1985). "Use of the Surgical Stapler to Obliterate the Left Atrial Appendage," Surgery, Gynecology & Obstetric 160:565-566.

Cohn et al., "Right thoracotomy, femorofemoral bypass, and deep hypothermia for re- replacement of the mitral valve" Ann Thorac Surg (1989) 48:69-71, © 1989 Society of Thoracic Surgeons, USA.

(56)          References Cited

OTHER PUBLICATIONS

Coselli et al., "Congenital intrapericardial aneurysmal dilatation of the left atrial appendage", Case Reports: The Annals of Thoracic Surgery, vol. 39, No. 5, May 1985, pp. 466-468.

Cox et al., "Five-Year Experience with the Maze Procedure for Atrial Fibrillation" Ann Thorac Surg (1993) 56:814-824.

Crystal et al., "Left Atrial Appendage Occlusion Study (LAAOS): A Randomized Clinical Trial of Left Atrial Appendage Occlusion During Routine Coronary Artery Bypass Graft Surgery for Long-term Stroke Prevention," Am Heart J (2003) 145:174-178, © 2003 Mosby, Inc., USA.

Dictionary.com definition for "adjacent" as accessed Oct. 17, 2023; https://www.dictionary.com/browse/adjacent, 5 pages.

Disesa et al., "Ligation of the Left Atrial Appendage Using an Automatic Surgical Stapler" Accepted for publication Jul. 26, 1988, Div. of Cardiac Surgery, Brigham and Women's Hospital, Boston, MA, 3 pages.

Examiner's Answer to Appeal Brief mailed on Jan. 28, 2021, for U.S. Appl. No. 15/874,257, filed Jan. 18, 2028, 20 pages.

Extended European Search Report for European Application No. 15843078.5 mailed Jan. 30, 2018, 16 pages.

Extended European Search Report for European Application No. 22195451.4 mailed Dec. 8, 2022, 11 pages.

Final Office Action for U.S. Appl. No. 14/549,811 dated Dec. 18, 2018, 18 pages.

Final Office Action for U.S. Appl. No. 14/549,811 dated May 13, 2020, 19 pages.

Final Office Action for U.S. Appl. No. 14/549,811 dated Sep. 5, 2017, 18 pages.

Final Office Action for U.S. Appl. No. 14/964,930 mailed Nov. 30, 2016, 17 pages.

Final Office Action for U.S. Appl. No. 15/868,270 mailed Dec. 9, 2019, 22 pages.

Final Office Action for U.S. Appl. No. 15/868,270 mailed Feb. 3, 2021, 22 pages.

Final Office Action for U.S. Appl. No. 17/841,760 mailed Aug. 30, 2023, 5 pages.

Final Office Action mailed on Apr. 4, 2024, for U.S. Appl. No. 18/342,481, filed Jun. 27, 2023, 13 pages.

Final Office Action mailed on Dec. 22, 2023, for U.S. Appl. No. 18/342,542, filed Jun. 27, 2023, 9 pages.

Final Office Action mailed on Feb. 27, 2024, for U.S. Appl. No. 18/342,519, filed Jun. 27, 2023, 9 pages.

Final Office Action mailed on Feb. 4, 2013, for U.S. Appl. No. 13/010,509, filed Jan. 20, 2011, 28 pages.

Final Office Action mailed on Feb. 5, 2019, for U.S. Appl. No. 14/585,712, filed Dec. 30, 2014, 21 pages.

Final Office Action mailed on Jan. 11, 2017, for U.S. Appl. No. 14/462,930, filed Aug. 19, 2014, 13 pages.

Final Office Action mailed on Jan. 26, 2023, for U.S. Appl. No. 16/536,936, filed Aug. 9, 2019, 18 pages.

Final Office Action mailed on Jun. 18, 2021, for U.S. Appl. No. 16/536,936, filed Aug. 9, 2019, 11 pages.

Final Office Action mailed on Jun. 22, 2020, for U.S. Appl. No. 15/874,257, filed Jan. 18, 2028, 15 pages.

Final Office Action mailed on May 27, 2020, for U.S. Appl. No. 15/904,541, filed Feb. 26, 2018, 12 pages.

Final Office Action mailed on Oct. 2, 2017, for U.S. Appl. No. 14/585,712, filed Dec. 30, 2014, 24 pages.

Final Rejection Office Action for U.S. Appl. No. 13/282,775 mailed on Aug. 21, 2014, 7 pages.

Final Rejection Office Action for U.S. Appl. No. 14/085,836 mailed on Dec. 23, 2016, 9 pages.

Final Rejection Office Action for U.S. Appl. No. 14/085,836 mailed on Nov. 24, 2015, 9 pages.

Fisher, D.C. et al. (Dec. 1998). "Large Gradient Across a Partially Ligated Left Atrial Appendage," Journal of the American Society of Echocardiography 11(12):1163-1165.

Fumoto et al., "A novel device for left atrial appendage exclusion: The third- generation atrial exclusion device" J Thorac Cardiov Surg (2008) 136:1019-27 © 2008 American Association for Thoracic Surgery, USA.

Ganeshakrishnan et al., "Congenital Intrapericardial Aneurysm of the Left-Atrial Appendage" Case Report: Thorac. Cardiovasc. Surgeon (1992) 40(6):382-384.

Garcia-Fernandez, M.A et al. (Oct. 1, 2003). "Role of Left Atrial Appendage Obliteration in Stroke Reduction in Patients With Mitral Valve Prosthesis," Journal of the American College of Cardiology 42(7):1253-1258.

Gillinov et al., "Stapled excision of the left atrial appendage" J Thorac Cardiovasc Surg (2005) 129:679-680.

Grundeman et al., "Experimental videothoracoscopic cannulation of the left atrial appendix" Surg Enclose (1993) 7:511-513, © 1993 Springer-Verlag New York, Inc., USA.

Halperin, J.L. et al. (Oct. 1, 2003). "Obliteration of the Left Atrial Appendage for Prevention of Thromboembolism," Journal of the American College of Cardiology 42(7):1259-1261.

Hoit, B.D. et al. (Jan. 1993). "Altered Left Atrial Compliance After Atrial Appendectomy. Influence on Left Atrial and Ventricular Filling," Circulation Research 72(1):167-175.

Hondo et al., "The Role of the Left Atrial Appendage; A Volume Loading Study in Open-chest Dogs" Jpn Heart J, Mar. 1995, pp. 225-234, Japan.

Johnson, W.D. et al. (2000). "The Left Atrial Appendage: Our Most Lethal Human Attachment! Surgical Implications," Euro. J. Cardiothoracic. Surg. 17:718-722.

Kamohara et al., "A novel device for left atrial appendage exclusion" J Thorac Cardiov Surg (2005) 130(6):1639-1644.

Kamohara et al., "Impact of left atrial appendage exclusion on left atrial function" J Thorac Cardiov Surg (2007) 133:174-81, © 2007 American Association for Thoracic Surgery, USA.

Kamohara, K. et al. (Aug. 2006). "Evaluation of a Novel Device for Left Atrial Appendage Exclusion: The Second-generation Atrial Exclusion Device," The Journal of Thoracic and Cardiovascular Surgery 132(2):340-346.

Katz, E.S. et al. (Aug. 2000). "Surgical Left Atrial Appendage Ligation is Frequently Incomplete: A Transesophageal Echocardiographic Study," Journal of the American College of Cardiology 36(2):468-471.

Kaymaz et al., "Location, Size and Morphological Characteristics of Left Atrial Thrombi as Assessed by Echocardiography in Patients with Rheumatic Mitral Valve Disease" Eur. J Echocardiography, vol. 2, Issue 4, Dec. 2001, pp. 270-276, © 2001 The European Society of Cardiology.

Landymore et al., "Staple Closure of the Left Atrial Appendage" The Canadian Journal of Surgery, vol. 27, No. 2, Mar. 1984, pp. 144-145.

Landymore, M.D., R. W., "Stapling of Left Atrial Appendage" to the Editor: Ann Thorac Surg (1989) 47:794. 2 pages.

Lindsay, B.D. (1996). "Obliteration of the Left Atrial Appendage: A Concept Worth Testing," The Annals of Thoracic Surgery 61:515. 1 page.

Lipkin et al., "Aneurysmal dilation of left atrial appendage diagnosed by cross sectional echocardiography and surgically removed" Br Heart J (1985) 53:69-71, National Heart Hospital, London, UK.

Lynch et al., "Recanalization of the Left Atrial Appendage Demonstrated by Transesophageal Echocardiography" Ann Thorac Surg (1997) 63:1774-1775.

Mole et al., "Desmoid Tumour in Thoractomy Scar 5 Years After Excision of a Left Giant Atrial Appendage Aneurysm in Female with a Family History of Gardner's Syndrome" Thorac Cardiovasc Surg 40 (1991) pp. 300-302, © 1992 Georg Thieme Verlag Stuttgart, New York.

Non-Final Office Action for U.S. Appl. No. 13/282,775 mailed on Feb. 25, 2014, 10 pages.

Non-Final Office Action for U.S. Appl. No. 14/085,836 mailed on Aug. 15, 2016, 7 pages.

Non-Final Office Action for U.S. Appl. No. 14/085,836 mailed on Jun. 17, 2015, 10 pages.

Non-Final Office Action for U.S. Appl. No. 14/085,836 mailed on Jun. 27, 2017, 6 pages.

(56)         References Cited

OTHER PUBLICATIONS

Non-Final Office Action for U.S. Appl. No. 14/549,811 dated Feb. 8, 2017, 18 pages.
Non-Final Office Action for U.S. Appl. No. 14/549,811 dated May 2, 2018, 17 pages.
Non-Final Office Action for U.S. Appl. No. 14/549,811 dated May 20, 2021, 20 pages.
Non-Final Office Action for U.S. Appl. No. 14/549,811 dated Oct. 28, 2019, 17 pages.
Non-Final Office Action for U.S. Appl. No. 14/964,930 mailed May 20, 2016, 23 pages.
Non-Final Office Action for U.S. Appl. No. 15/868,270 mailed Jul. 6, 2020, 22 pages.
Non-Final Office Action for U.S. Appl. No. 15/868,270 mailed Sep. 30, 2019, 18 pages.
Non-Final Office Action for U.S. Appl. No. 17/841,760 mailed Jul. 28, 2023, 10 pages.
Non-Final Office Action for U.S. Appl. No. 17/841,760 mailed May 14, 2024, 9 pages.
Non-Final Office Action mailed on Apr. 22, 2016, for U.S. Appl. No. 14/462,930, filed Aug. 19, 2014, 14 pages.
Non-Final Office Action mailed on Aug. 17, 2012, for U.S. Appl. No. 13/010,509, filed Jan. 20, 2011, 19 pages.
Non-Final Office Action mailed on Aug. 28, 2013, for U.S. Appl. No. 13/010,509, filed Jan. 20, 2011, 22 pages.
Non-Final Office Action mailed on Dec. 1, 2023, for U.S. Appl. No. 18/342,481, filed Jun. 27, 2023, 11 pages.
Non-Final Office Action mailed on Dec. 26, 2023, for U.S. Appl. No. 18/342,556, filed Jun. 27, 2023, 9 pages.
Non-Final Office Action mailed on Feb. 24, 2020, for U.S. Appl. No. 15/874,257, filed Jan. 18, 2028, 13 pages.
Non-Final Office Action mailed on Feb. 9, 2021, for U.S. Appl. No. 16/536,936, filed Aug. 9, 2019, 12 pages.
Non-Final Office Action mailed on Jan. 17, 2020, for U.S. Appl. No. 15/904,541, filed Feb. 26, 2018, 10 pages.
Non-Final Office Action mailed on Jan. 3, 2024, for U.S. Appl. No. 18/342,533, filed Jun. 27, 2023, 7 pages.
Non-Final Office Action mailed on Jul. 12, 2022, for U.S. Appl. No. 16/536,936, filed Aug. 9, 2019, 13 pages.
Non-Final Office Action mailed on Jun. 16, 2023, for U.S. Appl. No. 17/676,516, filed Feb. 21, 2022, 11 pages.
Non-Final Office Action mailed on Mar. 13, 2017, for U.S. Appl. No. 14/585,712, filed Dec. 30, 2014, 10 pages.
Non-Final Office Action mailed on May 17, 2018, for U.S. Appl. No. 14/585,712, filed Dec. 30, 2014, 35 pages.
Non-Final Office Action mailed on Oct. 23, 2023, for U.S. Appl. No. 18/342,519, filed Jun. 27, 2023, 11 pages.
Non-Final Office Action mailed on Sep. 11, 2023, for U.S. Appl. No. 18/342,556, filed Jun. 27, 2023, 10 pages.
Non-Final Office Action mailed on Sep. 12, 2023, for U.S. Appl. No. 18/342,566, filed Jun. 27, 2023, 10 pages.
Non-Final Office Action mailed on Sep. 8, 2023, for U.S. Appl. No. 18/342,542, filed Jun. 27, 2023, 12 pages.
Notice of Allowance for U.S. Appl. No. 13/282,775 mailed Dec. 11, 2014, 8 pages.
Notice of Allowance for U.S. Appl. No. 14/085,836 mailed Oct. 17, 2017, 9 pages.
Notice of Allowance for U.S. Appl. No. 14/549,811 dated Nov. 10, 2021, 11 pages.
Notice of Allowance for U.S. Appl. No. 14/964,930 mailed Jan. 11, 2018, 7 pages.
Notice of Allowance for U.S. Appl. No. 15/868,270 mailed Mar. 16, 2022, 8 pages.
Notice of Allowance for U.S. Appl. No. 18/342,519 mailed Jul. 15, 2024, 11 pages.
Notice of Allowance mailed on Apr. 10, 2024, for U.S. Appl. No. 18/342,542, filed Jun. 27, 2023, 11 pages.
Notice of Allowance mailed on Apr. 10, 2024, for U.S. Appl. No. 18/342,556, filed Jun. 27, 2023, 9 pages.
Notice of Allowance mailed on Apr. 19, 2024, for U.S. Appl. No. 18/342,566, filed Jun. 27, 2023, 12 pages.
Notice of Allowance mailed on Apr. 24, 2024, for U.S. Appl. No. 18/342,533, filed Jun. 27, 2023, 7 pages.
Notice of Allowance mailed on Dec. 28, 2023, for U.S. Appl. No. 18/342,566, filed Jun. 27, 2023, 13 pages.
Notice of Allowance mailed on Jun. 13, 2022, for U.S. Appl. No. 15/874,257, filed Jan. 18, 2028, 8 pages.
Notice of Allowance mailed on Mar. 25, 2014, for U.S. Appl. No. 13/010,509, filed Jan. 20, 2011, 15 pages.
Notice of Allowance mailed on May 23, 2019, for U.S. Appl. No. 14/585,712, filed Dec. 30, 2014, 11 pages.
Notice of Allowance mailed on May 9, 2024, for U.S. Appl. No. 18/342,542, filed Jun. 27, 2023, 11 pages.
Notice of Allowance mailed on Nov. 2, 2023, for U.S. Appl. No. 17/131,975, filed Dec. 23, 2020, 12 pages.
Notice of Allowance mailed on Oct. 20, 2017, for U.S. Appl. No. 14/462,930, filed Aug. 19, 2014, 10 pages.
Notice of Allowance mailed on Oct. 20, 2023, for U.S. Appl. No. 17/676,516, filed Feb. 21, 2022, 15 pages.
Notice of Allowance mailed on Oct. 23, 2023, for U.S. Appl. No. 18/342,508, filed Jun. 27, 2023, 8 pages.
Notice of Allowance mailed on Sep. 18, 2020, for U.S. Appl. No. 15/904,541, filed Feb. 26, 2018, 8 pages.
Odell, J.A. et al. (1996). "Thorascopic Obliteration of the Left Atrial Appendage: Potential for Stroke Reduction?" Ann. Thorac. Surg. 61:565-569.
Omari et al., "Effect of right atrial appendectomy on the release of atrial natriuretic hormone" J Thorac Cardiovasc Surg (1991) 102:272-279, USA.
PCT/US2006/027553 Prelim Report w/ Written Opinion Jan. 16, 2008 Medical Ltd, 7 pages.
PCT/US2009/051270 Prelim Rprt on PATBL, Atricure, Inc., Feb. 3, 2011. 7 pages.
PCT/US2012/051002 Intl Search Report w/ Written Opinion Oct. 23, 2012 Atricure, Inc., 10 pages.
Riley et al., "Mitral Valve Repair" CTSNET Experts' Techniques, doc 5729, pp. 1-7, (2004).
Robin et al., Strangulation of the Left Atrial Appendage through a Congenital Partial Pericardial Defect, Chest, 67:3, Mar. 1975, pp. 354-355.
Rosenzweig et al., "Thromboembolus from a Ligated Left Atrial Appendage" J Am Soc Echocardiography, vol. 14, pp. 396-398, May 2001, © 2001 American Society of Echocardiography, USA.
Salzberg et al., "Left atrial appendage clip occlusion: Early clinical results" J Thorac Cardiov Surg (2010) vol. 139, No. 5, pp. 1269-1274.
Salzberg, S.P. et al. (2008). "Surgical Left Atrial Appendage Occlusion: Evaluation of a Novel Device with Magnetic Resonance Imaging," European Journal of Cardiothoracic Surgery 34:766-770.
Stollberger, C. et al. (2007). "Leave the Left Atrial Appendage Untouched for Stroke Prevention!" Journal of Thoracic and Cardiovascular Surgery 134(2):549-550.
Stollberger, C. et al. (Dec. 2003). "Elimination of the Left Atrial Appendage to Prevent Stroke or Embolism ?: Anatomic, Physiologic, and Pathophysiologic Considerations," 124(6):2356-2362.
Stollberger et al., "Is left atrial appendage occlusion useful for prevention of stroke or embolism in atrial fibrillation?" Z Kardiol 91:376-379 (2002).
Stollberger et al., "Stroke Prevention by Means of Left Atrial Appendage Strangulation?" to the Editor: J Thorac Cardiovasc Surg (2010) 140(3): p. 732.
Tabata, T. et al. (Feb. 1, 1998). "Role of Left Atrial Appendage in left Atrial Reservoir Function as Evaluated by Left Atrial Appendage Clamping During Cardiac Surgery," The American Journal of Cardiology 81:327-332.
Thomas, TV, "Left atrial appendage and valve replacement" Am Heart Journal, vol. 84, No. 6, Dec. 1972, pp. 838-839.
Unknown, Endowrist Instruments and Accessories Catalog, Intuitive Surgical, Sunnyvale, California, Sep. 2005. 11 pages.
Unknown, Surgical procedure report to track prior art with regards to a minimally invasive left atrial appendage exclusion, Jan. 1, 2007, USA. 2 pages.

(56) References Cited

OTHER PUBLICATIONS

Unknown, "Transesophageal Echocardiographic Correlates of Thromboembolism in High Risk Patients with Nonvalvular Atrial Fibrillation" The American College of Physicians, Apr. 1998, pp. 639-647, © 1998 American College of Physicians, USA.

Veinot et al., "Anatomy of the Normal Left Atrial Appendage: A Quantitative Study of Age-Related Changes in 500 autopsy hearts: implications for echocardiographic examination" Circulation (1997) 96: 3112-3115, USA.

Wakabayashi, MD., "Expanded applications of diagnostic and therapeutic thoracoscopy" J. Thorac Cardiovasc Surg (1991) 102:721-723.

Wudel, J.H. et al. (Apr. 3, 2008). "Video-Assisted Epicardial Ablation and left Atrial Appendage Exclusion for Atrial Fibrillation: Extended Follow-Up," The Annals of Thoracic Surgery 85:34-38.

Notice of Allowance mailed on Sep. 29, 2024, for U.S. Appl. No. 18/342,519, filed Jun. 27, 2023, 8 pages.

* cited by examiner

376

376

376

376

OCCLUSION CLIP

CROSS-REFERENCE TO RELATED APPLICATIONS

The present application is a continuation of U.S. application Ser. No. 17/841,760, filed Jun. 16, 2022, which is a continuation of U.S. application Ser. No. 15/868,270, filed Jan. 11, 2018, now U.S. Pat. No. 11,389,175, which is a continuation of U.S. application Ser. No. 14/964,930, filed Dec. 10, 2015, now U.S. Pat. No. 9,901,352, which claims the benefit of U.S. Provisional Application No. 62/091,230, filed Dec. 12, 2014, each of which is hereby incorporated by reference in its entirety.

INTRODUCTION TO THE INVENTION

The present disclosure is directed to occlusion clips and, more specifically, to implantable open-ended occlusion clips. In exemplary form, the exemplary occlusion clips may be utilized to occlude the left atrial appendage.

It is a first aspect of the present invention to provide an occlusion clip comprising: (a) a first elongated occlusion arm; (b) a second elongated occlusion arm; (c) a first elongated biasing arm coupled to a distal portion of the first elongated occlusion arm; (d) a second elongated biasing arm coupled to a distal portion of the second elongated occlusion arm, where a proximal portion of the first elongated biasing arm is coupled to a proximal portion of the second elongated biasing arm, where the first elongated occlusion arm extends parallel to the first elongated bias arm along a majority of its length, and where the second elongated occlusion arm extends parallel to the second elongated bias arm along a majority of its length.

In a more detailed embodiment of the first aspect, the first elongated occlusion arm includes a free proximal end, and the second elongated occlusion arm includes a free proximal end. In yet another more detailed embodiment, the first elongated occlusion arm includes a first convex tissue engaging surface, the second elongated occlusion arm includes a second convex tissue engaging surface, and the first convex tissue engaging surface faces the second convex tissue engaging surface. In a further detailed embodiment, a portion of the first convex tissue engaging surface lies along a first plane, a portion of the second convex tissue engaging surface lies along a second plane, and the first plane and the second plane are parallel to one another. In still a further detailed embodiment, no portion of the first convex tissue engaging surface extends through the second plane, and no portion of the first convex tissue engaging surface extends through the second plane. In a more detailed embodiment, the first elongated occlusion arm includes a first longitudinal length, the second elongated occlusion arm includes a second longitudinal length, more than seventy five percent of the first longitudinal length includes a first gap interposing the first elongated occlusion arm and the first elongated biasing arm, and more than seventy five percent of the second longitudinal length includes a second gap interposing the second elongated occlusion arm and the second elongated biasing arm. In a more detailed embodiment, the first elongated biasing arm includes a third longitudinal length, the second elongated biasing arm includes a fourth longitudinal length, the third longitudinal length is greater than the first longitudinal length, and the fourth longitudinal length is greater than the second longitudinal length.

In yet another more detailed embodiment of the first aspect, the first elongated occlusion arm, the second elongated occlusion arm, the first elongated biasing arm, and the second elongated biasing arm are integral. In yet another more detailed embodiment, the occlusion clip further includes a fabric covering at least a portion of the occlusion clip. In a further detailed embodiment, the fabric covering comprises a tube that concurrently circumscribes at least one of: (a) the first elongated occlusion arm and the first elongated biasing arm; and (b) the second elongated occlusion arm and the second elongated biasing arm. In still a further detailed embodiment, the tube that concurrently circumscribes both: (a) the first elongated occlusion arm and the first elongated biasing arm; and (b) the second elongated occlusion arm and the second elongated biasing arm. In a more detailed embodiment, the occlusion clip includes a first distal cavity interposing a distal end of the first elongated occlusion arm and a distal end of the first elongated biasing arm, and the occlusion clip includes a second distal cavity interposing a distal end of the second elongated occlusion arm and a distal end of the second elongated biasing arm. In a more detailed embodiment, the occlusion clip includes a first proximal cavity interposing a proximal end of the first elongated occlusion arm and a proximal section of the first elongated biasing arm, the occlusion clip includes a second proximal cavity interposing a proximal end of the second elongated occlusion arm and a distal section of the second elongated biasing arm, a first bridge interposes the first proximal cavity and the first distal cavity, the first bridge linking the first elongated occlusion arm and the first elongated biasing arm, and a second bridge interposes the second proximal cavity and the second distal cavity, the second bridge linking the second elongated occlusion arm and the second elongated biasing arm.

It is a second aspect of the present invention to provide an occlusion clip comprising a continuous length of material interposing a pair of terminal ends, the continuous length of material including a first turn having a greater than 150 degree change of direction, a second turn having a second turn having a greater than 150 degree change of direction, a third turn having a greater than 150 degree change of direction, where the third turn occurs at a proximal end of the occlusion clip, where the first and second turns occur proximate a distal end of the occlusion clip, where the proximal end and the distal end are opposite one another, and where the pair of terminal ends occur proximate the proximal end of the occlusion clip.

In a more detailed embodiment of the second aspect, the first, second, and third turns lie within a common plane. In yet another more detailed embodiment, at least two of the first turn, the second turn, and the third turn lie within a common plane. In a further detailed embodiment, the first turn couples a first elongated occlusion arm to a first elongated biasing arm, the second turn couples a second elongated occlusion arm to a second elongated biasing arm, the third turn couples the first elongated biasing arm to the second elongated biasing arm, at least one of the first and second elongated occlusion arms interposes the first and second elongated biasing arms.

It is a third aspect of the present invention to provide a method of fabricating an occlusion clip comprising: (a) cutting out an outline of an occlusion clip precursor from a sheet of material, the occlusion clip precursor including a pair of occlusion arms and a pair of biasing arms; and, (b) compressing the occlusion clip precursor to preload a pair of occlusion arms to form an occlusion clip.

In a more detailed embodiment of the third aspect, the step of cutting out the outline is performed using electrical discharge machining. In yet another more detailed embodiment, the electrical discharge machining includes wire electrical discharge machining. In a further detailed embodiment, the method further includes wrapping the occlusion clip in a fabric. In still a further detailed embodiment, the fabric comprises a fabric tube that promotes tissue ingrowth. In a more detailed embodiment, the occlusion clip comprises a continuous length of material interposing a pair of terminal ends, the continuous length of material including a first turn having a greater than 150 degree change of direction, a second turn having a second turn having a greater than 150 degree change of direction, a third turn having a greater than 150 degree change of direction, where the third turn occurs at a proximal end of the occlusion clip, where the first and second turns occur proximate a distal end of the occlusion clip, where the proximal end and the distal end are opposite one another, and where the pair of terminal ends occur proximate the proximal end of the occlusion clip.

DETAILED DESCRIPTION

Figures 1, 2:
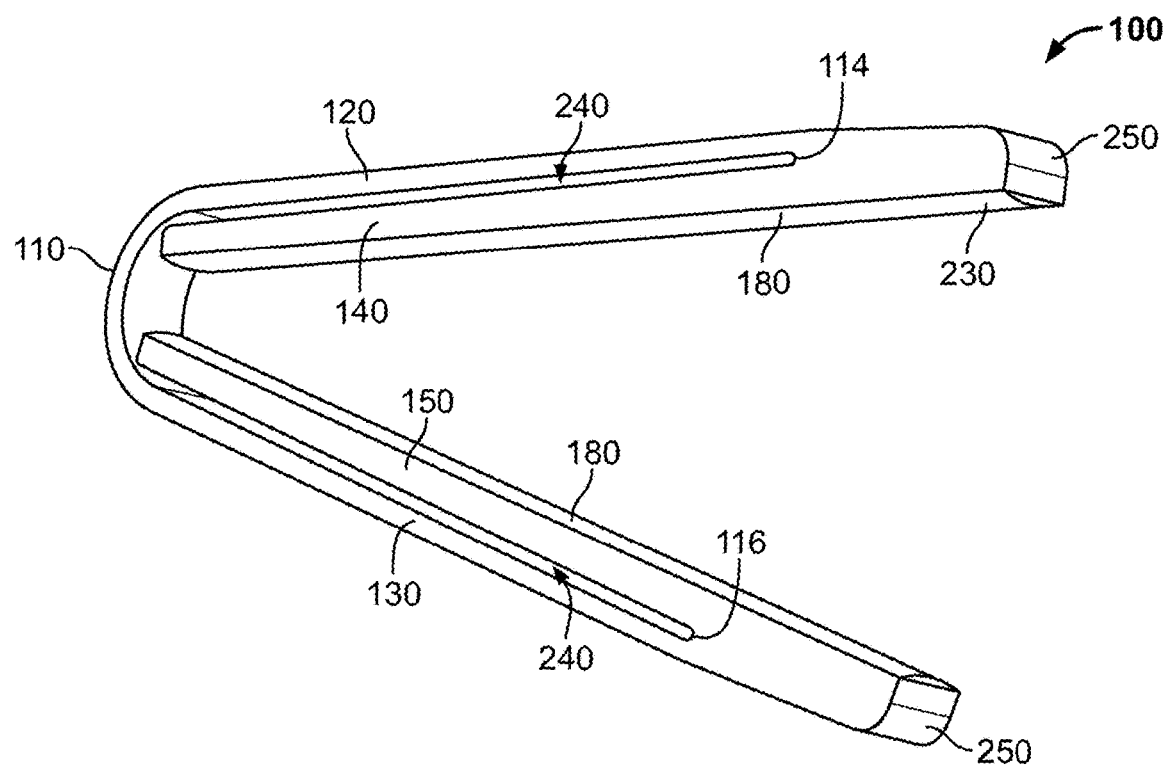
FIG. 1 is an elevated perspective view of a first exemplary occlusion clip in accordance with the instant disclosure shown in an open position.
FIG. 2 is a profile view of the first exemplary occlusion clip of FIG. 1 shown in an open position.

The exemplary embodiments of the present disclosure are described and illustrated below to encompass various aspects of implantable open-ended occlusion clips and methods of implanting open-ended occlusion clips to occlude the left atrial appendage. Of course, it will be apparent to those of ordinary skill in the art that the embodiments discussed below are exemplary in nature and may be reconfigured without departing from the scope and spirit of the present disclosure. However, for clarity and precision, the exemplary embodiments as discussed below may include optional steps, methods, and features that one of ordinary skill should recognize as not being a requisite to fall within the scope of the present disclosure.

Referencing FIGS. 1-4, a first exemplary occlusion clip 100 that may be used to occlude a left atrial appendage comprises a unitary body that may be fabricated from titanium using titanium sheet stock. A more detailed description of the process utilized to fabricate this first exemplary occlusion clip 100 will be discussed in a later section.

By way of an exemplary coordinate system, a thickness of the exemplary occlusion clip is taken along a Z-axis. Perpendicular to this Z-axis is a Y-axis and an X-axis (that is also perpendicular to the Y-axis). In exemplary form, the height of the occlusion clip 100 is taken along the Y-axis, while a longitudinal length (dominant dimension) of the occlusion clip 100 is taken along the X-axis.

In exemplary form, the occlusion clip 100 includes a U-shaped section 110 that is integrally coupled to a pair of elongated biasing/spring arms 120, 130. Each elongated biasing arm 120, 130 is integrally coupled to its own elongated occlusion arm 140, 150 that extends toward the U-shaped section 110. In particular, the U-shaped section 110 comprises a first turn 112 having a change of direction between approximately 145 to 215 degrees measured between the pair of elongated biasing arms 120, 130. Moreover, the transition between the first elongated biasing arm 120 and the first elongated occlusion arm 140 comprises a second turn 114 having a change of direction between approximately 145 to 215 degrees measured between the first elongated biasing arm 120 and the first elongated occlusion arm 140. Similarly, the transition between the second elongated biasing arm 130 and the second elongated occlusion arm 150 comprises a third turn 116 having a change of direction between approximately 145 to 215 degrees measured between the second elongated biasing arm 130 and the second elongated occlusion arm 150.

Each elongated occlusion arm 140, 150 is substantially rigid (i.e., inflexible) and includes a terminal end 160, with the terminal ends comprising the beginning and end of a course of material constituting the exemplary occlusion clip 100. In this exemplary embodiment, each occlusion arm 140, 150 includes a tissue engaging surface 180 that is convex. In exemplary form, the convex nature of the tissue engaging surface 180 is substantially constant along a longitudinal length (dominant dimension along the X-axis) of a respective occlusion arm 140, 150. More specifically, the profile of the tissue engaging surface 180 embodies an arc of a circle.

Interposing the tissue engaging surface 180 is a pair of planar surfaces 210 that are uniformly spaced apart from one another. For purposes of explanation with respect to this first exemplary embodiment, the thickness of titanium material (in the Z-direction) comprising the U-shaped section 110, the elongated biasing arms 120, 130, and the elongated occlusion arms 140, 150 (but for the tissue engaging surfaces 180) is constant. The arcuate profile of the tissue engaging surfaces 180 decreases the thickness of the occlusion clip 100 (in the Z-direction) until reaching zero at an apex 230. In other words, the apex 230 of each tissue engaging surface 180 occurs midway along a thickness dimension of the occlusion clip (i.e., in the Z-direction, midway between the planar surfaces 210) so that in the closed position (shown in FIG. 4) the tissue engaging surfaces 180 are parallel to one another and the apexes contact one another or are spaced apart from one another a uniform distance.

Each planar surface 210 defines a respective opposing lateral boundary of the occlusion clip 100. In this exemplary embodiment, the height of the planar surfaces 210 partially outlining the U-shaped section 110 (taken normal to the outer peripheral surface 260 is the interior surface 300) at the apex is approximately twenty-five percent (25%) greater than the height of the elongated biasing arms 120, 130 (taken normal to the outer peripheral surface 260 is the interior surface 320), which is substantially constant along the longitudinal length of the elongated biasing arms until proximate the turns 114, 116. This twenty-five percent (25%) increase in height decreases linearly until reaching zero percent change where the U-shaped section 110 meets the linear elongated biasing arms 120, 130. At the second and third turns 114, 116, the height of the planar surface 210 is maximized. In other words, the height of the planar surface 210 at the end of the turns 114, 116 is approximately equal to the height of the elongated biasing arms 120, 130, in addition to the height of the occlusion arms 140, 150, in addition to the height of a gap 240 between the elongated biasing arms 120, 130 and the occlusion arms 140, 150. This maximum height of the planar surfaces 210 decreases abruptly when extending proximally along the elongated occlusion arms 140, 150. In particular, the height of the planar surfaces 210 decreases linearly along the length of the elongated occlusion arms 140, 150 until reaching a minimum height proximate the terminal end 160. In contrast, when moving distally, the maximum height of the planar surfaces 210 decreases slightly until reaching a distal end 250. Proximate the distal end 250, the height of the planar surfaces 210 decreases and the profile changes embodying the curvature of a circle until reaching the distal end.

The distal end 250 is partially defined by an outer peripheral surface 260 that interposes the planar surfaces 210. In exemplary form, the height of this peripheral surface 260 is constant (in the Z-direction), consistent with the constant thickness of the clip 100. At the distal end, the peripheral surface 260 is planar, but takes on an arcuate curvature that tracks the circle curvature of the planar surfaces. This arcuate curvature leads into a planar distal segment 270 is joined to a planar proximal segment 280 near the second and third turns 114, 116. The proximal planar segment 280 joins a curved section 290, the curvature of which changes depending upon whether the clip 100 is in an open or closed position. Opposite the outer peripheral surface 260 is an interior surface 300.

The interior surface 300 cooperates with the planar surfaces 210, the outer peripheral surface 260, and the tissue engaging surfaces 180 to delineate the exterior boundary surfaces of the clip 100. In particular, the interior surface 300 includes a curved section 310, the curvature of which changes depending upon whether the clip 100 is in an open or closed position. This curved section 310 transitions into a pair of elongated planar biasing arm sections 320 that respectively join U-shaped curves 330, one for each turn 114, 116. Each U-shaped curve 330 is also joined to a respective elongated planar occlusion arm section 340. Two terminal ends 160 of the elongated biasing arms 120, 130 are delineated by corresponding blunt surfaces that include a rounded-over portion 350 that transition into a respective elongated planar occlusion arm section 340.

Figure 3:
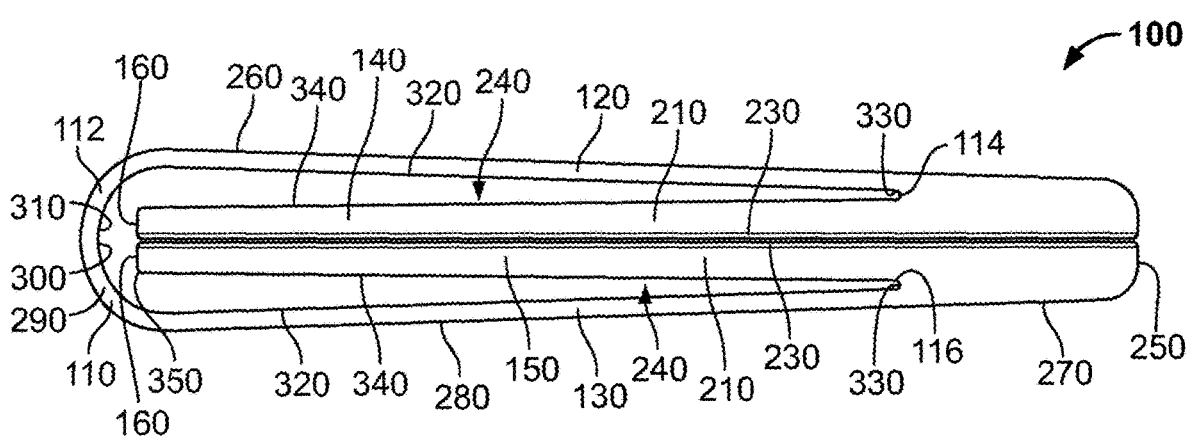
FIG. 3 is a profile view of the first exemplary occlusion clip of FIG. 1 shown in a closed position.
Figure 4:
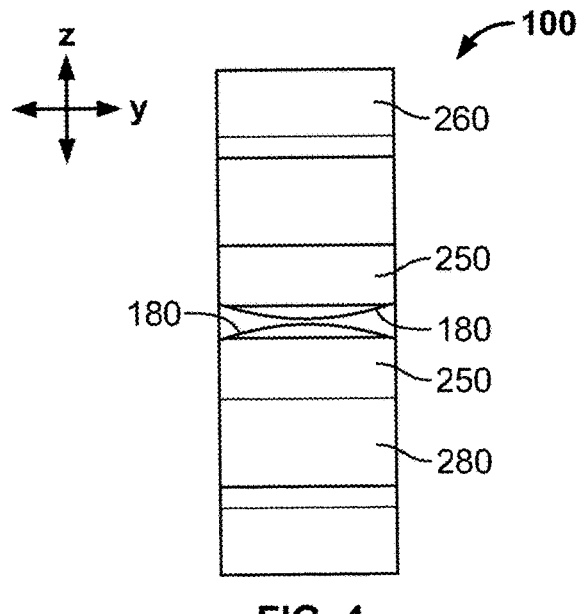
FIG. 4 is an end view of the first exemplary occlusion clip of FIG. 1 shown in a closed position.

As shown in FIGS. 3 and 4, the clip 100 takes on a closed position when nothing interposes the elongated biasing arms 120, 130. In this closed position, the elongated biasing arms 120, 130 abut one another. More specifically, the tissue engaging surfaces 180 are minimally spaced apart or contact one another. In addition, the gap 240 between the elongated biasing arms 120, 130 and the occlusion arms 140, 150 is more pronounced toward the U-shaped section 110. In other words, the elongated biasing arms 120, 130 are not parallel to the occlusion arms 140, 150. But this is not necessarily the case when the clip 100 takes on an open position.

Referring back to FIGS. 1-4, any position beyond the closed position is generally referred to as an open position. For purposes of discussion, and depicted in exemplary form, the fully open position corresponds to the elongated biasing arms 120, 130 oriented in parallel to the occlusion arms 140, 150, but the spacing (i.e., gap 240 width) between the distal portions of the proximal portions of the occlusion arms 140, 150 (proximate the second and third turns 114, 116) is several multiples of the spacing between the proximal portions of the occlusion arms 140, 150 (proximate the terminal ends 160). In this fully open position, the clip 100 may be configured to receive a left atrial appendage (LAA) in between the tissue engaging surfaces 180. More specifically, when in the fully open position, the clip 100 is moved along the base of the LAA (parallel with the dominant dimension of the LAA base) so that the LAA can be captured between the tissue engaging surfaces 180 without going over the top of the LAA It should be noted that the elongated biasing arms 120, 130 have an aspect ratio that is thinner in the Y-direction to allow for bending of the arms in the Y-direction, but is thicker in the Z-direction to retard the distal ends 250 of the clip 100 from separating in the Z-direction.

Figure 5:
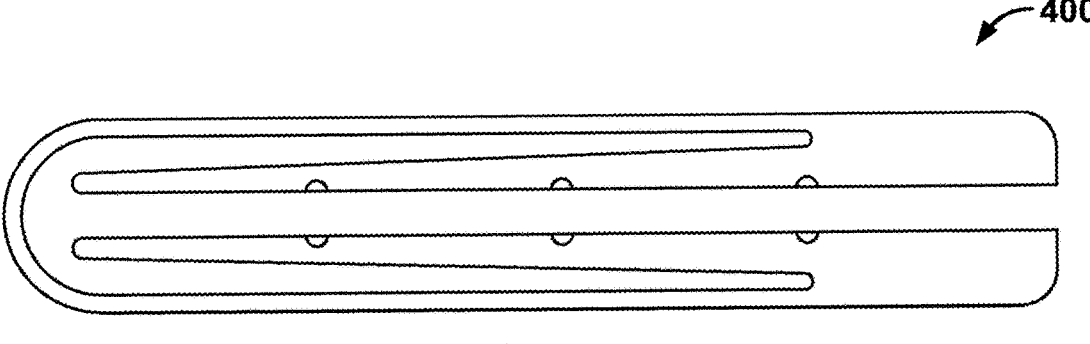
FIG. 5 is a profile view of a precursor to the first exemplary occlusion clip of FIG. 1.
Figure 6:
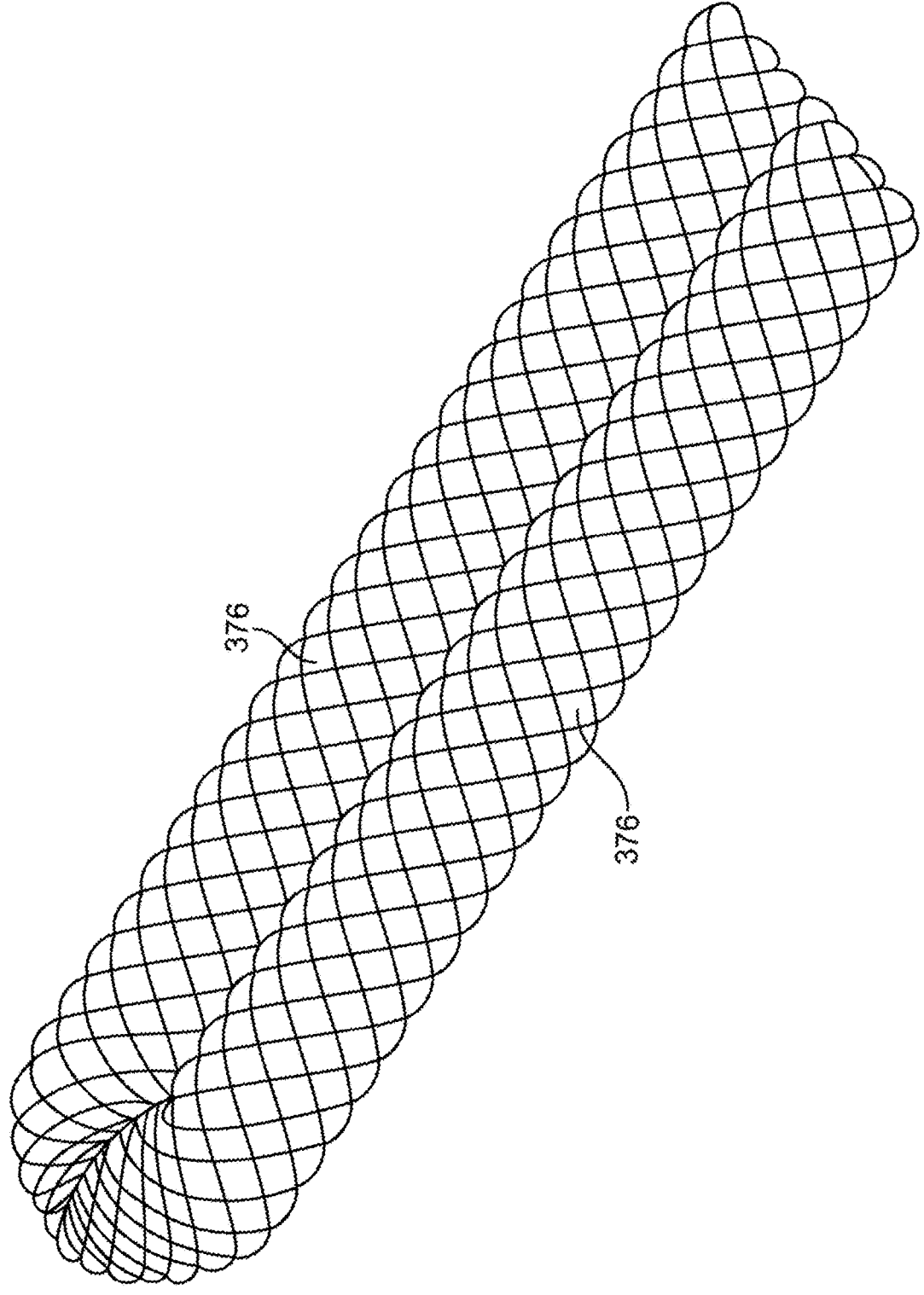
FIG. 6 is an elevated perspective view of the first exemplary occlusion clip of FIG. 1 shown in a closed position and covered by a fabric tube.

Referring to FIGS. 5 and 6, the exemplary clip 100 may be fabricated in various ways. By way of example, the exemplary clip 100 fabrication will be discussed in the context of wire electrical discharge machining (WEDM). In exemplary form, two or more sheets of an implantable grade titanium material (e.g. grade 2, grade 5), with each sheet having a thickness dimension of ⅛ inch and having length and width dimensions (e.g., 12 inch×12 inch, 18 inch×12 inch, etc.), are stacked upon one another along the thickness dimension and submerged within a dielectric bath, which may comprise deionized water. By way of example, the stacked sheets of titanium comprise a first electrode and the wire electrical discharge machine includes a second electrode comprising a spooled material (e.g., brass wire). Those skilled in the art are familiar with WEDM and, accordingly, a detailed description of WEDM has been omitted in furtherance of brevity.

Using WEDM, the outline of a precursor to the exemplary clip 100 shown in FIG. 5 is concurrently cut through each of the titanium sheets, thereby fabricating concurrently the same number of clips as there are sheets. After the outline of the precursor is cut, the wire electrical discharge machine repositions the second electrode with respect to the titanium sheets to form the outline of another precursor at locations previously uncut. This process is repeated until the wire electrical discharge machine exhausts the uncut locations where the exemplary precursor can be cut.

Subsequent to WEDM, each precursor clip (which all have the same shape and dimensions) is subjected to a tissue engaging surface step. In exemplary form, the tissue engaging surface step machines away material from the occlusion arms 140, 150 (that previously had a block C-shaped profile; i.e. rectangular profile) to form the arcuate profile of the tissue engaging surfaces 180.

Subsequent to the tissue engaging surface step, each precursor clip (which all have the same shape and dimensions) is subjected to a compression step. In exemplary form, the compression step establishes the dimension of any gap interposing the tissue engaging surface 180, as well as any preload (i.e., the amount of force required to separate the tissue engaging surfaces from one another presuming no gap is present between the tissue engaging surfaces post compression step) exhibited by the clip 100. In this exemplary process, the precursor is compressed proximate the U-shaped section 110, which causes the tissue engaging surfaces 180 to move toward one another. For example, the U-shaped section may be compressed approximately 0.38 inches, which results in zero gap between the tissue engaging surfaces 180 and a preload of approximately 1.5 pounds of force (i.e., 1.5 pounds of force or greater is required to separate the engaging surfaces 180 from one another). The compression step results in a closing force on the occlusion arms 140, 150 that is essentially constant from the distal to the proximal end especially between the fully closed position and an open position exhibiting a four millimeter opening/gap. In this fashion, the elongated biasing arms 120, 130 are substantially elastic, but the U-shaped section 110 is substantially non-elastically deformed. Moreover, depending upon the length of the clip 100 (in the X-direction), the amount of force required to open the clip may change. In a circumstance where the target force at two millimeters of opening/gap between the occlusion arms 140, 150 approximately 0.032 pounds per millimeter of occlusion member length, this may result in different amounts of clamping force applied to the U-shaped section 110 of the clip 100 depending upon its length. For example, in the context of a fifty millimeter clip 100, the compression may impart a preload of approximately 1.6 pounds, whereas in the context of a thirty-five millimeter clip the preload may be reduced to 1.12 pounds (where a greater pound preload requires a greater extent of compression). After the precursor is compressed proximate the U-shaped section 110, the exemplary clip 100 fabrication is complete and the clip components take on the preloaded positions shown in FIGS. 3 and 4.

In this first exemplary embodiment, the clip 100 may exhibit a uniform force across the length of the occlusion arms 140, 150. In particular, the uniform force may be applied across the length of the occlusion arms 140, 150 between one to four millimeters opening, for example. This uniform force profile along the length of the occlusion arms 140, 150 coincides with common compressed thicknesses of a majority of left atrial appendages. For example, data has shown that a compressed left atrial appendage, sufficient to occlude without severing, has a thickness on the order to of two millimeters, plus-or-minus one millimeter. Accordingly, a clip exerting a uniform force profile within a range of one to four millimeters would encompass a majority of patient left atrial appendages subjected to occlusion compression. To the extent that uniform force is not exactly obtainable across the length of the occlusion arms 140, 150, it should be noted that the clip 100 may be preloaded to more heavily toward the distal end 250 of the clip to encourage tissue clamped between the occlusion arms from squeezing out beyond the distal end.

As shown in FIG. 6, in further exemplary form, the exemplary clip 100 may be encapsulated using a fabric tube 376 that may be fabricated from any of various materials operative to allow biologic tissue ingrowth such as, without limitation, polyethylene terephthalate and expanded polytetrafluoroethylene. In particular, the fabric tube 376 may be treated with collagen, albumin, etc., to promote tissue ingrowth. In this exemplary embodiment, a passage extends through the fabric tube, with opposing openings at the ends of the tube demarcating the beginning and end respectively of the passage. By way of example, one opening of the fabric tube 376 circumscribes one of the distal ends 250 of the clip 100 and is moved proximally along the length of the elongated biasing arm 120 and the elongated occlusion arm 140 to circumscribe both concurrently. Continued proximal movement of the fabric tube 376 eventually reaches the terminal end 160 of the elongated occlusion arm 140 and the U-shaped section 110, where the fabric tube follows the shape of the U-shaped section 110 and reaches the terminal end 160 of the elongated occlusion arm 150. At this point, the opening of the fabric tube 376 is repositioned distally to concurrently circumscribe the elongated biasing arm 130 and the elongated occlusion arm 150. Continued distal movement of the fabric tube 376 eventually results in the end of the fabric tube passing slightly beyond the distal end 250 of the elongated biasing arm 130 and the elongated occlusion arm 150, whereby the entire clip is housed within the passage of the fabric tube. The fabric tube 376 includes corresponding ends that extend beyond the distal ends 250 of the occlusion clip 100 a sufficient length to allow the corresponding ends to be sewn shut. The ends may be sewn shut after the fabric tube 376 has been positioned around the clip 100, or one end of the fabric tube may be sewn shut prior to positioning the fabric tube around the clip. Nevertheless, after the fabric tube 376 has been positioned around the clip 100, the sewn ends of the fabric tube operate enclose the clip within the fabric tube.

Figure 7:
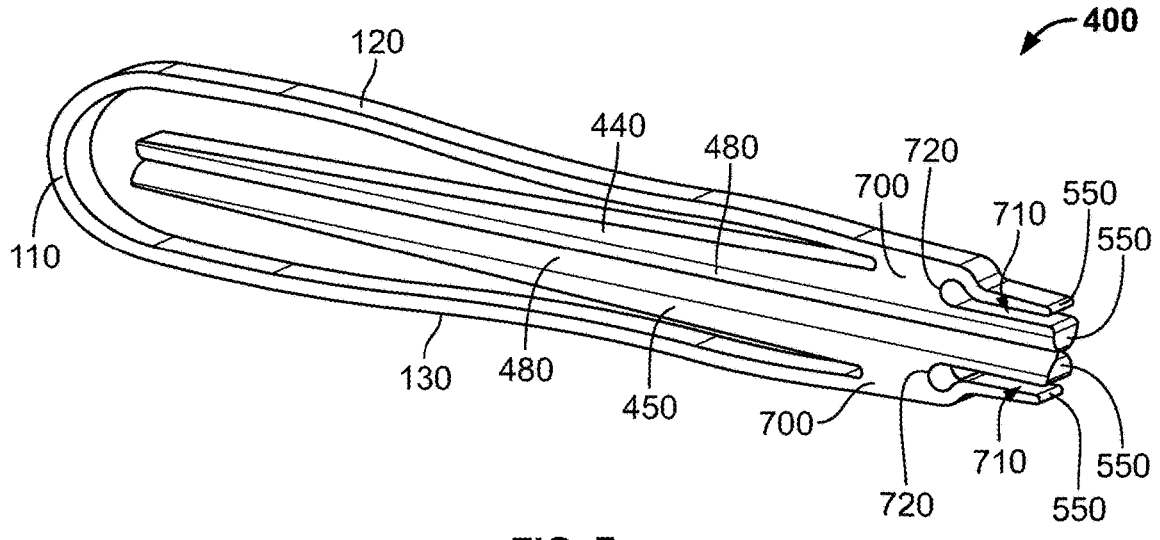
FIG. 7 is an elevated perspective view of a second exemplary occlusion clip in accordance with the instant disclosure shown in a closed position.
Figure 8:
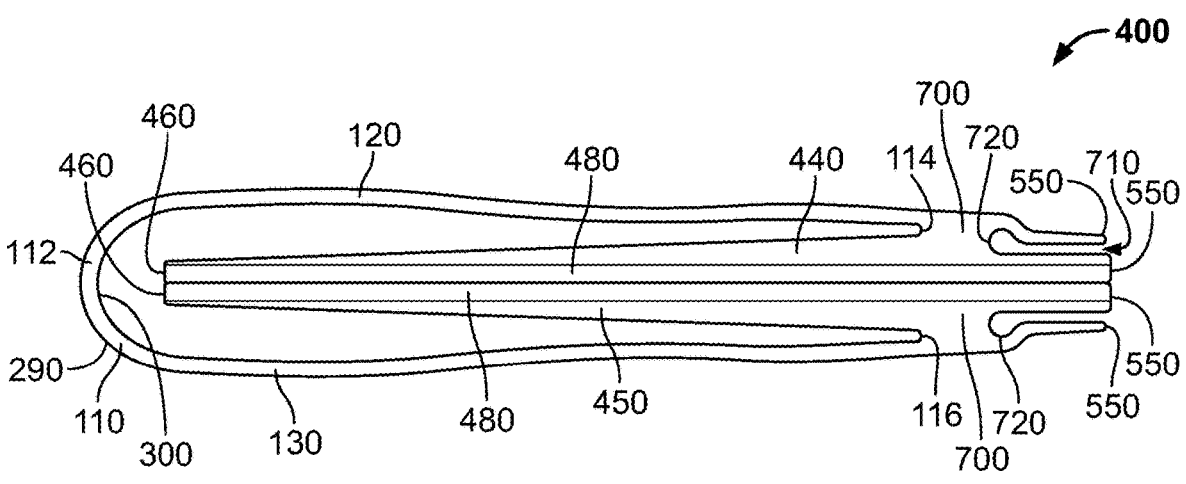
FIG. 8 is a profile view of the second exemplary occlusion clip of FIG. 7 shown in a closed position.
Figures 9, 10:
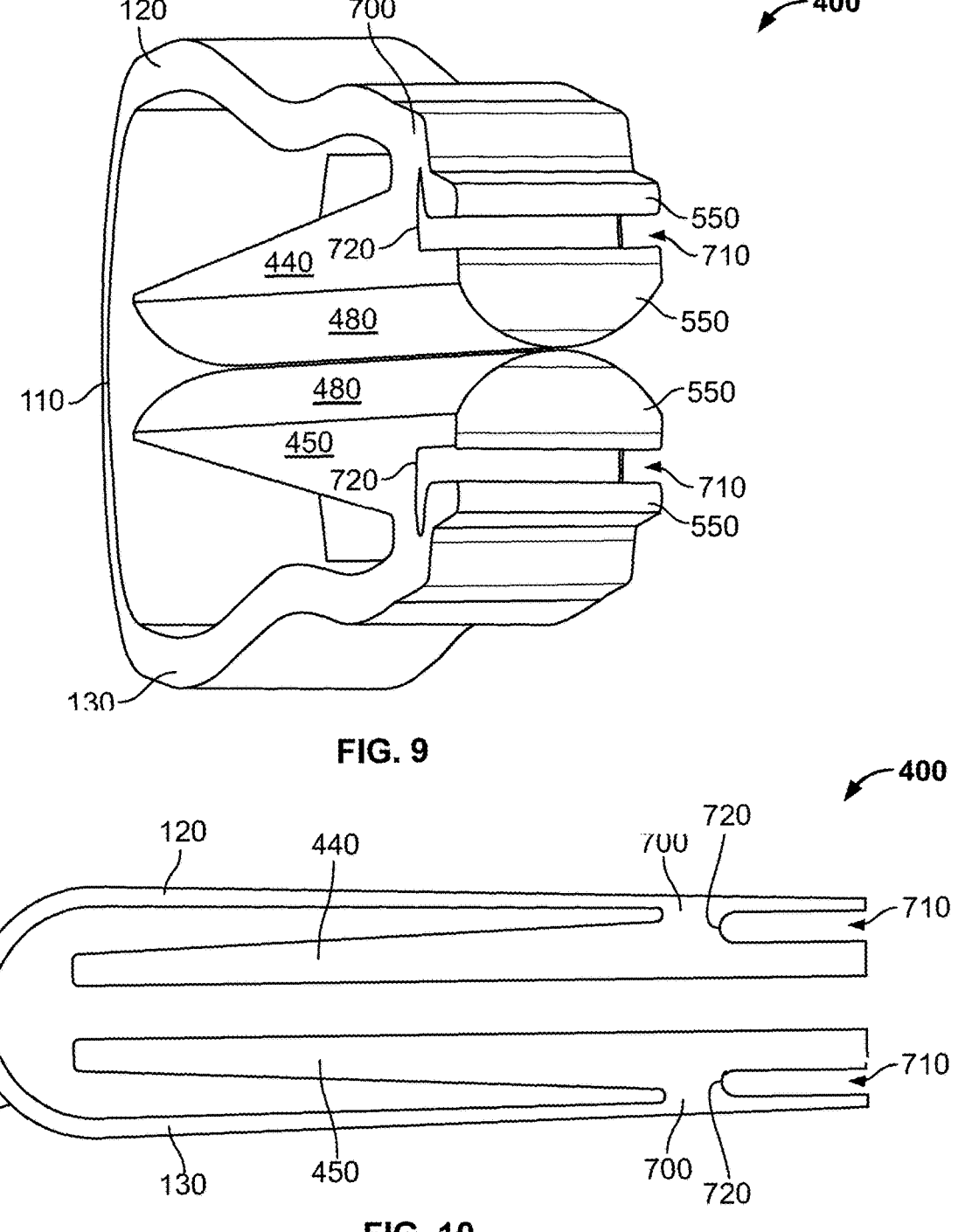
FIG. 9 is a perspective end view of the second exemplary occlusion clip of FIG. 7 shown in a closed position.
FIG. 10 is a profile view of a precursor to the second exemplary occlusion clip of FIG. 7.

Referencing FIGS. 7-9, a second exemplary occlusion clip 400 also comprises a unitary body that may be fabricated from titanium using titanium sheet stock. As will be discussed in more detail hereafter, this second exemplary occlusion clip 400 may be fabricated in a similar manner to the first exemplary occlusion clip 100.

For purposes of explanation, this second exemplary occlusion clip 400 has many features that are in common with the first exemplary occlusion clip 100. Consequently, a detailed discussion of these common features has been omitted in furtherance of brevity, but will be apparent from the common reference numerals present in the accompanying drawings for this second exemplary occlusion clip 400.

This second exemplary occlusion clip 400 differs in part from the first exemplary occlusion clip 100 by having occlusion arms 440, 450 that do not have a uniform height between a proximal end 460 and the second turn 114 or third turn 116. Instead, the height (in the Y-direction) of the occlusion arms 440, 450 decreases linearly in a proximal direction from the second/third turn 114/116 until reaching the proximal end 460.

In addition, the second exemplary occlusion clip 400 differs from the first exemplary occlusion clip 100 by having tissue engaging surfaces 480 with a different arcuate profile. In exemplary form, the tissue engaging surfaces 480 have an arcuate profile that corresponds to the arc of a circle having a substantially smaller diameter than the arcuate profile of the tissue engaging surfaces 180 that corresponds to the arc of a circle having a much larger diameter. In this fashion, the height (in the Y-direction) of the tissue engaging surfaces 480 is substantially greater than that of the tissue engaging surfaces 180 of the first exemplary clip 100.

Yet another distinction between the second exemplary occlusion clip 400 and the first exemplary occlusion clip 100 is the distal ends 250, 550. Initially, as shown in FIG. 10, the distal ends 550 of the occlusion clip 400 precursor each include a U-shaped recess 710 that operates to divide the distal ends of the elongated biasing arms 120, 130 from the distal ends of the occlusion arms 440, 450 so that a bridge portion 700 connects a respective elongated biasing arm 120, 130 to a respective occlusion arm 440, 450. In exemplary form, the height of the U-shaped recess 710 in the occlusion clip 400 precursor is substantially constant and tapers at a distal end 720 until reaching zero, indicative of the U-shaped profile.

Similar to the first exemplary occlusion clip 100, this second exemplary occlusion clip may also be fabricated using WEDM. In exemplary form, two or more sheets of an implantable grade titanium material (e.g. grade 2, grade 5), with each sheet having a thickness dimension of ⅛ inch and having length and width dimensions (e.g., 12 inch×12 inch, 18 inch×12 inch, etc.), are stacked upon one another along the thickness dimension and submerged within a dielectric bath, which may comprise deionized water. By way of example, the stacked sheets of titanium comprise a first electrode and the wire electrical discharge machine includes a second electrode comprising a spooled material (e.g., brass wire). Using WEDM, the outline of a precursor to the exemplary clip 400 shown in FIG. 10 is concurrently cut through each of the titanium sheets, thereby fabricating concurrently the same number of clips as there are sheets. After the outline of the precursor is cut, the wire electrical discharge machine repositions the second electrode with respect to the titanium sheets to form the outline of another precursor at locations previously uncut. This process is repeated until the wire electrical discharge machine exhausts the uncut locations where the exemplary precursor can be cut.

Subsequent to WEDM, each precursor clip (which all have the same shape and dimensions) is subjected to a crimping step. In exemplary form, the distal ends 550 of the elongated biasing arms 120, 130 and the occlusion arms 440, 450 are crimped to deform the distal end of each elongated biasing arms 120, 130. As shown in FIGS. 7-9, the result of the crimping step is deformation of the elongated biasing arms 120, 130 to reduce the height of the U-shaped recess 710, with the exception of the proximal end 720. Though not required, the crimping step may create uniform spacing between the distal portions of the occlusion arms 440, 450 and the elongated biasing arms 120, 130. As will be discussed in more detail hereafter, the crimping step is operative to reshape the U-shaped recess 710 in order to retain portions of the fabric tube 376.

Subsequent to WEDM, each precursor clip (which all have the same shape and dimensions) is also subjected to a tissue engaging surface step. In exemplary form, the tissue engaging surface step machines away material from the occlusion arms 440, 450 (that previously had a block C-shaped profile; i.e. rectangular profile) to form the arcuate profile of the tissue engaging surfaces 480.

Further subsequent to WEDM, each precursor clip (which all have the same shape and dimensions) is subjected to a compression step. In exemplary form, the compression step establishes the dimension of any gap interposing the tissue engaging surface 480, as well as any preload exhibited by the clip 400. In this exemplary process, the precursor is compressed midway between the U-shaped section 110 and the distal ends 550 (by compressing the elongated biasing arms 120, 130), which causes the tissue engaging surfaces 480 to move toward one another. For example, the elongated biasing arms 120, 130 may be compressed approximately 0.38 inches, which results in zero gap between the tissue engaging surfaces 480 and a preload of approximately 1.5 pounds of force (i.e., 1.5 pounds of force or greater is required to separate the engaging surfaces 480 from one another). In other words, after the precursor is compressed, the exemplary clip 400 fabrication is complete and the clip components take on the preloaded positions shown in FIGS. 7-9.

Figure 11:
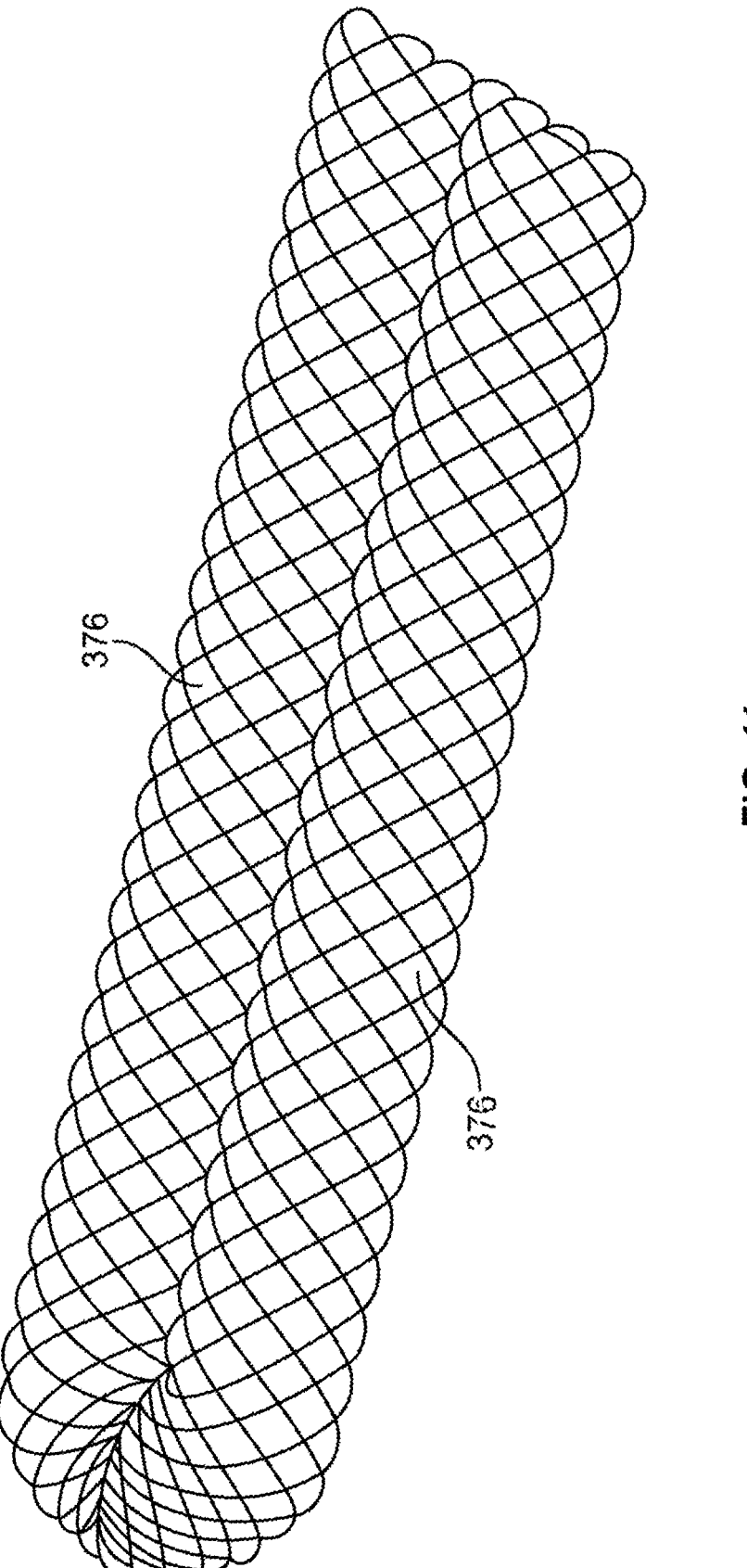
FIG. 11 is an elevated perspective view of the second exemplary occlusion clip of FIG. 7 shown in a closed position and covered by a fabric tube.

As shown in FIG. 11, in further exemplary form, the exemplary clip 400 may be encapsulated using a fabric tube 376 that may be fabricated from any of various materials operative to allow biologic tissue ingrowth such as, without limitation, polyethylene terephthalate and expanded polytetrafluoroethylene. In particular, the fabric tube 376 may be treated with collagen, albumin, etc., to promote tissue ingrowth. In this exemplary embodiment, a passage extends through the fabric tube, with opposing openings at the ends of the tube demarcating the beginning and end respectively of the passage. By way of example, one opening of the fabric tube 376 circumscribes one of the distal ends 550 of the clip 400 and is moved proximally along the length of the elongated biasing arm 120 and the elongated occlusion arm 440 to circumscribe both concurrently. Continued proximal movement of the fabric tube 376 eventually reaches the terminal end 460 of the elongated occlusion arm 440 and the U-shaped section 110, where the fabric tube follows the shape of the U-shaped section 110 and reaches the terminal end 460 of the elongated occlusion arm 450. At this point, the opening of the fabric tube 376 is repositioned distally to concurrently circumscribe the elongated biasing arm 130 and the elongated occlusion arm 450. Continued distal movement of the fabric tube 376 eventually results in the end of the fabric tube passing slightly beyond the distal end 550 of the elongated biasing arm 130 and the elongated occlusion arm 450, whereby the entire clip is housed within the passage of the fabric tube. The fabric tube 376 includes corresponding ends that extend beyond the distal ends 550 of the occlusion clip 100 a sufficient length to allow the corresponding ends to be tucked into the crimped U-shaped recess 710. The dimensions of each crimped U-shaped recess 710 are such that tucking a respective end of the fabric tube into each recess and thereafter crimping a distal portion of the U-shaped recess 710 (as discussed above pursuant to the crimping step) operates to retain the ends of the fabric tube within the U-shaped recess 710 via a friction fit. In this manner, contrary to the other exemplary embodiment, the ends of the fabric tube 376 are not sewn shut.

The foregoing exemplary fabric attachment may provide advantages over the other exemplary method that sews shut the fabric loop ends. By way of example, by securing the distal ends of the fabric to the distal ends of the clip 400, rotation of the fabric tube about the clip is retarded.

Following from the above description, it should be apparent to those of ordinary skill in the art that, while the methods and apparatuses herein described constitute exemplary embodiments of the present disclosure, the invention contained herein is not limited to these precise embodiments and that changes may be made to such embodiments without departing from the scope of the invention as defined by the claims. Additionally, it is to be understood that the invention is defined by the claims and it is not intended that any limitations or elements describing the exemplary embodiments set forth herein are to be incorporated into the interpretation of any claim element unless such limitation or element is explicitly stated. Likewise, it is to be understood that it is not necessary to meet any or all of the identified advantages or objects of the invention disclosed herein in order to fall within the scope of any claims, since the invention is defined by the claims and since inherent and/or unforeseen advantages of the claimed invention may exist even though they may not have been explicitly discussed herein.

The invention claimed is:

1. An occlusion clip comprising:

a first arm and a second arm, the first and second arms each include a linear occlusion surface extending along a majority of a longitudinal dimension thereof, the linear occlusion surface extending to a distal end of the occlusion clip, each of the first arm and the second arm including a pair of free terminal ends;

a spring longitudinally overlapping itself and the first and second arms, where the longitudinal dimension is the dominant dimension, the spring operatively coupled to the first and second arms and biasing the first and second arms toward one another to impart a preload to the occlusion clip, the spring including a pair of free terminal ends; and a pair of bridges each, respectively, separating one free terminal end of the spring from one free terminal end of one of the first and second arms proximate the distal end of the occlusion clip, each of the pair of bridges interposing a longitudinally extending distal cavity and a longitudinally extending proximal cavity.

2. The occlusion clip of claim 1, wherein the preload is greater at the distal end of the occlusion clip than a proximal end of the occlusion clip.

3. The occlusion clip of claim 1, wherein the preload is about 1.12 pounds to about 1.6 pounds.

4. The occlusion clip of claim 1, wherein the spring comprises a first turn with a change of direction between about 145 degrees to about 215 degrees.

5. The occlusion clip of claim 4, wherein the spring comprises a second turn having a change of direction between about 145 degrees to about 215 degrees.

6. The occlusion clip of claim 5, wherein the spring comprises a third turn having a change of direction between about 145 degrees to about 215 degrees.

7. The occlusion clip of claim 1, wherein a curvature of the spring when the occlusion clip is in a closed configuration is different from when the occlusion clip is in an open configuration.

8. The occlusion clip of claim 1, wherein each of the first and second arms is substantially rigid.

9. The occlusion clip of claim 1, wherein the distal end of each of the first and second arms comprises a rounded portion.

10. The occlusion clip of claim 1, wherein each of the first and second arms comprises a tissue engaging surface.

11. The occlusion clip of claim 10, wherein the tissue engaging surfaces are closer to one another when the occlusion clip is in a closed configuration compared to an open configuration.

12. The occlusion clip of claim 10, wherein each tissue engaging surface is convex along at least a portion thereof.

13. The occlusion clip of claim 1, wherein the occlusion clip is configured to receive at least a portion of a left atrial appendage through the distal end thereof when in an open configuration.

14. The occlusion clip of claim 1, wherein at least a portion of the clip comprises titanium.

15. The occlusion clip of claim 1, wherein the spring forms a proximal end of the occlusion clip.

16. The occlusion clip of claim 1, wherein the spring extends longitudinally along a majority of each of the first and second arms.

17. An occlusion clip comprising:

a first arm including a first linear occlusion surface and a second arm including a second linear occlusion surface overlapping the first linear occlusion surface, the first and second linear occlusion surfaces having opposing longitudinal ends and extending along a majority of a longitudinal dimension of the first and second arms, wherein the longitudinal dimension is the dominant dimension, wherein the first and second arms are repositionable with respect to one another between a closed position and an open position where the first and second linear occlusion surfaces are spaced from one another, and wherein thicknesses of the first and second arms in a direction perpendicular to the longitudinal dimension decrease linearly from distal portions of the first and second arms to proximal portions of the first and second arms; and a spring operatively coupled to the first and second arms, wherein the first and second arms each terminate with a free end within a proximal cavity delineated by the spring, wherein the spring exerts a preload to direct the first and second arms toward the closed position, and wherein the preload is higher at second longitudinal ends, opposite the first longitudinal ends, of the first and second arms.

18. An occlusion clip comprising:

a first arm including a first linear occlusion surface and a second arm including a second linear occlusion surface overlapping the first linear occlusion surface, the first and second linear occlusion surfaces extending proximally to distally along a majority of a longitudinal dimension of the first and second arms, wherein the longitudinal dimension is the dominant dimension, wherein the first and second arms are repositionable with respect to one another between a closed position and an open position where the first and second linear occlusion surfaces are spaced from one another; and a pair of bridges that vertically interpose, perpendicular to the longitudinal dimension, a spring and the first and second arms to connect the first and second arms to the spring, wherein a first free terminal end of the spring and a free terminal end of the first arm extend from a first of the pair of bridges to delineate a first longitudinally distally open cavity, and a second free terminal end of the spring and a free terminal end of the second arm extend from a second of the pair of bridges to delineate a second longitudinally distally open cavity.

* * * * *